United States Patent [19]

Hollander

[11] 4,041,617
[45] Aug. 16, 1977

[54] APPARATUS AND METHOD FOR INDICATION AND MEASUREMENT OF SIMULATED EMOTIONAL LEVELS

[76] Inventor: James Fisher Hollander, 40 Middlesex St., Matawan, N.J. 07747

[21] Appl. No.: 708,560

[22] Filed: July 26, 1976

[51] Int. Cl.² .............................................. G09B 19/00
[52] U.S. Cl. .................................................... 35/22 R
[58] Field of Search ............. 35/22 R, 24 C; 235/184, 235/185

[56] References Cited

U.S. PATENT DOCUMENTS

| | | | |
|---|---|---|---|
| 2,297,011 | 9/1942 | Mooney | 35/24 C |
| 3,406,281 | 10/1968 | Buchanan et al. | 35/24 C UX |
| 3,418,729 | 12/1968 | Ravich | 35/22 R |
| 3,491,194 | 1/1970 | Smith | 35/24 C |
| 3,748,750 | 7/1973 | Viemeister | 35/22 R |
| 3,839,804 | 10/1974 | Amend et al. | 35/24 C X |
| 3,971,142 | 7/1976 | Hollander | 35/22 R |

OTHER PUBLICATIONS

"Depression: Causes and Treatment" by A. T. Beck, U. of Pennsylvania Press, p. 7, 1967.
"A Computer Experiment in Elementary Social Behavior", by J. T. Gullahorn et al., IEEE Transactions on Systems Science and Cybernetics, vol. 55c-1, No. 1, pp. 45-51, 1965.
"Motivation System for a Robot" by J. Koplowitz et al., IEEE Transactions on Systems, Man and Cybernetics, July 1973, pp. 425-428.
"Punish/Reward: Learning with a Critic in Adaptive Threshold Systems" by B. Widrow et al., IEEE Transactions on Systems, Man and Cybernetics, vol. SMC-3, No. 5, pp. 455-457; 1973.
"The Phillips/Newlyn Hydraulic Model", by W. T. Newlyn, Yorkshire Bulletin of Economic and Social Research, vol. 2, No. 2, 1950, pp. 111-127.
"Conditioning Illustrated by an Automatic Mechanical Device", The American Journal of Psychology, vol. XLII, 1930, pp. 110-111.
"The Aboutness of Emotions" by R. M. Gordon, American Philosophical Quarterly, vol. II, No. I, 1974, p. 27.

*Primary Examiner*—William H. Grieb

[57] ABSTRACT

Adjustment dials are attached to adjustable sources of physical force interpretable by the dials as positive and negative decisional influences. One or more of the physical forces are measured by one or more emotional level indicators which also display type or polarity of emotion based on a comparison between the forces provided by comparing apparatus. The comparing apparatus also drives a decision indicator.

The apparatus disclosed in detail is alternatively of electronic, fluidic, and mechanical nature. Emotions measured are Emotional Tension, Bad-Good Feelings, Guilt-Pride, and Like-Dislike. Subjective and objective disagreement indications are also derived. The apparatus may be used for simulating interpersonal relationships. A Contrary-Agreeable Attitude selector switch is incorporated in a perceptual processing circuit for use in such apparatus.

70 Claims, 14 Drawing Figures

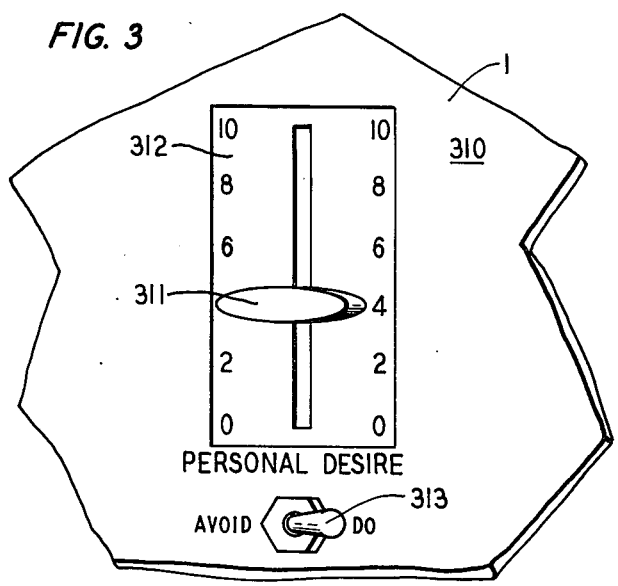
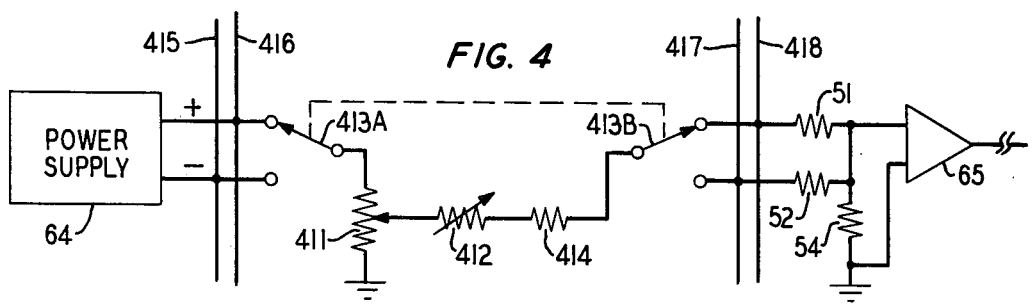
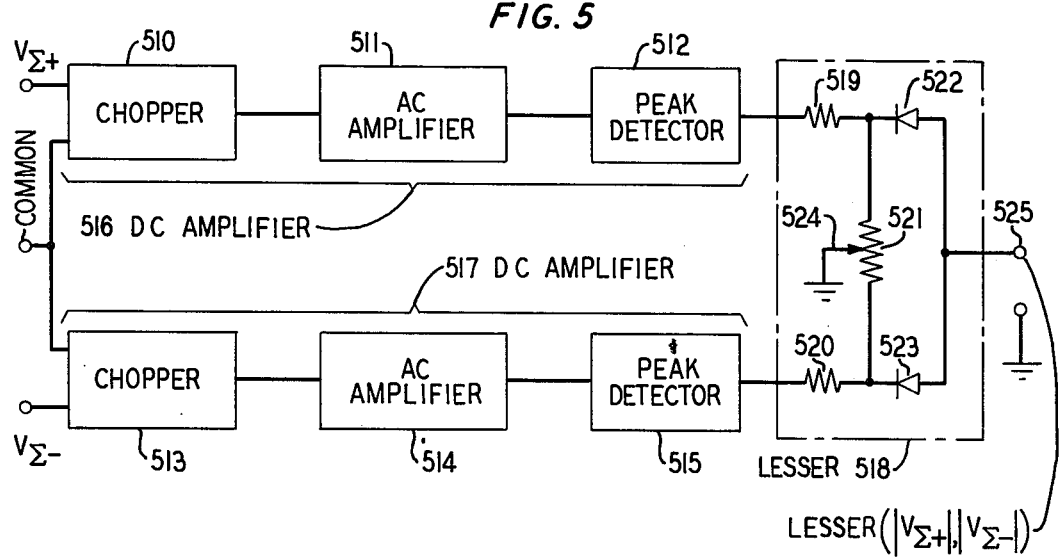

APPARATUS AND METHOD FOR INDICATION AND MEASUREMENT OF SIMULATED EMOTIONAL LEVELS

BACKGROUND OF THE INVENTION

The present invention relates to simulation apparatus which indicates emotions. More specifically, the present invention involves derivation and/or measurement of quantities analogous to emotions in simulation apparatus.

Mankind's desire to more fully know itself and to solve personal and interpersonal problems is age old. The Judeo-Christian tradition has for centuries grappled with the complexities of life alone and in relationship and offers a vision of historically unfolding triumph of vital life in which every human creative power may participate. At the present historical moment the passionless life is feeling the influence of passionate yearnings and awarenesses. A new awareness of the emotional life and of the potentialities of relationship is abroad. Concepts of emotion and even emotionally "hot" cognition are in ferment in the intellectual world.

In recent years the search for emotional understanding has been extended into the area of simulation apparatus having features which provide information about personal and interpersonal behavior. For example, U.S. Pat. No. 3,748,750 issued to P.E. Viemeister on July 31, 1973, illustrates a type of electronic simulator of human behavior including logic circuitry which is selectively adjustable to represent human characteristics on a relative value scale. Encoded representations of human situational stimuli are inputted to the simulator through a card reader. Visual output indicators represent a plurality of different behavioral responses to the input stimuli.

Multiple position switches are set to various needs, emotions, fears, loves, and attitudes. In this manner the ways in which various stimuli and emotions affect decisions are made more evident.

In the present inventor's own work, decision-making and interpersonal relationship simulation have been important concerns. See his U.S. Pat. Applications "Simulation Apparatus" Ser. No. 580,308 filed May 23, 1975, now U.S. Pat. No. 3,971,142, issued July 27, 1976, and "Apparatus for Simulation of Interpersonal Relationships and Activity" Ser. No. 628,830 filed Nov. 4, 1975, now U.S. Pat. No. 4,009,525, issued Mar. 1, 1977.

However, an aspect of human experience is that many emotions seem to be related to or even caused by situations, stimuli, attitudes, and other emotions. Furthermore, many emotions can have continuously varying degree so that means other than multiple position switches would be preferable for demonstrating them. On the other hand, emotions are known to change abruptly. These considerations lead to a problem: How can simulation apparatus be configured so that emotional analogs are measured within a simulation apparatus itself? How can a simulation machine be constructed so that it produces or derives quantities or indications that can be considered analogous to or indicative of emotions in living beings?

SUMMARY OF THE INVENTION

The present invention is an approach to an answer to these questions. In the invention, what a being does, or decides, is recognized as being influenced by decisional influences including desires or motivations which can have a continuous range of levels. The levels are interrelated with emotions which correspond to them, and the emotions are also related to decisions and actions, or memories thereof, of self and others. The invention accordingly provides physical apparatus having adjustment dials for indicating and varying physical analogs of decisional influences, means for comparing the levels with each other or with actions of self or others, and one or more indicators for displaying measured emotional levels dependent upon the action or calculations of the comparing means and upon the decisional influence analogs.

Correspondingly, in the method aspects of the invention performed by the apparatus of the invention, physical analogs of decisional influences having magnitudes and polarity are generated, then compared and finally an emotional analog is produced and indicated to have a magnitude depending on the magnitude of at least one of the decisional influences and the result of the comparing operation.

The invention can find application in psychology, social psychology, philosophy, theology, the professions, the humanities, and other branches of knowledge. Theories of emotion can be illustrated and tested by means of the present invention. Research, teaching, and learning of subject matter related to the aforementioned fields is facilitated by its use. The invention may also be used as a means of self-expression and counselling in a clinical setting, and as a fascinating tool for self-education and for personal and emotional growth in other contexts.

The present invention will be more perfectly understood by a consideration of a few of the numerous embodiments thereof shown in the appended drawing.

BRIEF DESCRIPTION OF THE DRAWING

FIG. 3 is a pictorial diagram of an alternative panel assembly for an adjustment means including an adjustment dial and switch relating to magnitude and type of Personal Desire decisional influence.

FIG. 4 is a partially block, partially schematic diagram of an alternative electrical circuit portion that obviates any need for a diode network in FIG. 2B.

FIG. 5 is a partially block, partially schematic diagram of an alternative electrical circuit for deriving a nervous tension output without need of circuitry utilizing a relay as in FIG. 2B, for the purpose.

THEORY EXAMPLE

Figure 1:
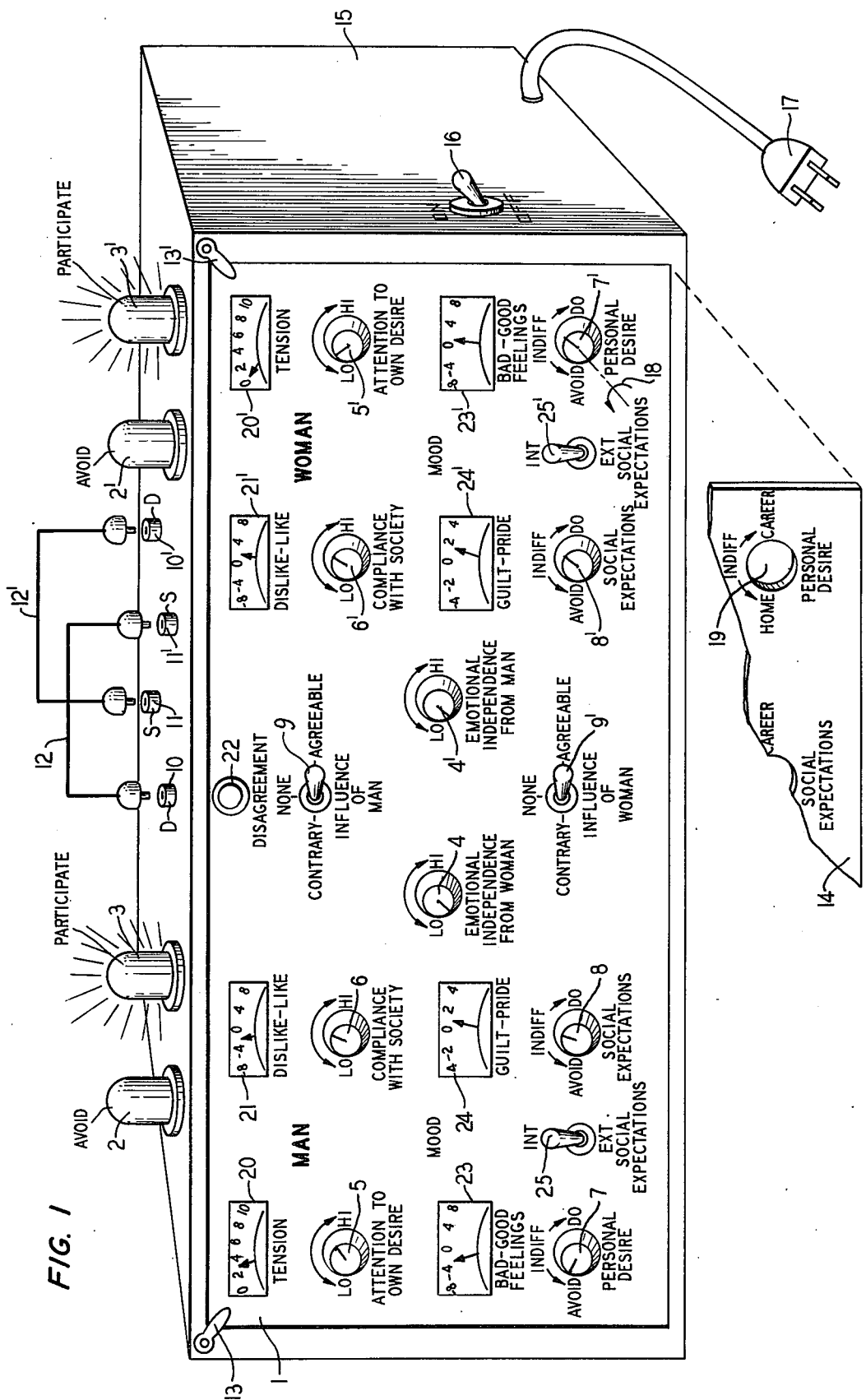
FIG. 1 is a pictorial view of the exterior of apparatus according to the invention for simulating a man-woman relationship, the apparatus including emotion-measuring meters for good-bad feelings, guilt and pride, emotional conflict or tension, and like and dislike of the other person, as well as a disagreement indicator. The FIG. 1 apparatus includes two distinct simulators, one for a man and one for a woman.

The embodiments of the invention in general can be used to illustrate fundamental theoretical understandings of the individual alone and in relationship. However, it is to be understood that the invention in its full scope is not to be identified with any specific detailed theoretical construction, but rather the invention in one aspect of its utility can be a means of communicating specific theories through specific embodiments. For convenience in suggesting this aspect of the application of the invention, a specific theory example is hereinbelow presented to accompany the later description of specific apparatus embodiments of the invention.

DECISIONS AND DESIRES

When a decision is being made let there be two choices, A and not-A, that is, logically opposite or complementary alternatives. Let a decision variable D be defined for person $i$ such that $$D_i = \begin{cases} +1 \text{ if decision made is A} \\ -1 \text{ if decision made is not-A} \end{cases} \quad (1)$$

Individual $i$ is under the influence of a variety of decisional influence pressures which are exerted when a decision is made. Let each decisional influence $j$ on individual $i$ be denoted by a real variable U such that $$U_{ij} = \begin{cases} \text{Positive, if there is desire for A} \\ \text{Zero, if there is no desire relevant} \\ \text{Negative, if there is desire for not-A} \end{cases} \quad (2)$$

According to the present theory example the decisionmaker "weighs" the decisional influences and the decision reached depends upon the outcome of the weighing process. For instance, if all the decisional influences are for a decision A then the decision will in fact be A. Conversely, if all the decisional influences are for the decision not-A, then the decision will be not-A. If some of the decisional influences are positive and others are negative then the preponderant weight sum will determine the character of the decision. If all of the influences are absent, $U_{ij} =$ Zero, then the decision is not defined in terms of A or not-A. In mathematical terms the decision D is related to the decisional influences $U_{ij}$ by the formula $$D_i = \text{SIGN}(\sum_j U_{ij}) \quad (3)$$

where the SIGN function is defined as $$\text{SIGN}(x) = \begin{cases} +1 \text{ if } x \text{ exceeds zero} \\ \text{undefined if } x = 0 \\ -1 \text{ if } x \text{ is less than zero} \end{cases} \quad (4)$$

The decisional influences $U_{ij}$ are conveniently associated with particular decisional influences of common experience, although alternative names or additional qualitative differences may be recognized. For example, let the decisional influences $U_{ij}$ include $U_{i1}$, a personal desire decisional influence, (5)

$U_{i2}$, a social pressure decisional influence, (6)

and $U_{i3}$, a decisional influence due to a single influential other person such as a close friend, romantic partner, leader, or employer. (7)

Each decisional influence $U_{ij}$ may be recognized as being the result of two components $E_{ij}$ and $W_{ij}$ associated with the basic pressure and the weight given to that pressure or isolation from that pressure, respectively. In other words $$U_{ij} = E_{ij} W_{ij} \quad (8)$$

For example, the basic personal desire $E_{i1}$ can be thought of as the deepseated, real, or even unconscious personal desire in favor of a particular decision. The weight $W_{i1}$ given to the basic personal desire may be thought of as an aspect of the personality of the individual or as related to repression of the basic desire. The basic pressures $E_{i2}$ and $E_{i3}$ may be thought of as conventional, real, or objective influences due to society and specific other individuals which are weighted in proportions $W_{i2}$ and $W_{i3}$ by the individual in the course of decisionmaking in accordance with his or her personality. Thus, another way of describing the decisionmaking process is $$D_i = \text{SIGN}(\sum_j E_{ij} W_{ij}) \quad (9)$$

This formula relates basic situational factors $E_{ij}$ and personality factors $W_{ij}$ to decisionmaking $D_i$ of individual $i$. If the situational factors $E_{ij}$ be considered part of a situation defined by the vector (10)

-continued $$E_i = \begin{bmatrix} E_{i1} \\ E_{i2} \\ E_{i3} \end{bmatrix}$$

impinging upon a personality defined by the vector $$W_i = \begin{bmatrix} W_{i1} \\ W_{i2} \\ W_{i3} \end{bmatrix} \tag{11}$$

then the decision reached is related to the inner product of the situation vector (10) and personality vector (11) by the formula (equivalent to (9))

$$D_i = \text{SIGN}(\overline{E_i W_i}) \tag{12}$$

In some contexts it may be helpful to think of the $E_{ij}$ as being the lengths of orthogonal vectors in a space of dimensionality N equal to the number of decisional factors $E_i$ which are being considered. Then the decisional alternatives presented correspond to halves of a line knifing through the origin of the N-space, the line being composed of half-lines corresponding to the logically exclusive decision alternatives. The line knifes through the N-space with a particular direction characteristic of the decision to be made by the individual personality relative to the situation. The projections of the decisional influence vectors upon the decision line are equal in magnitude to the $U_{ij}$, the $W_{ij}$ are direction cosines, and the vector sum of the projections compared to the half-lines determines the character of the decision.

When $E_{i3}$ is the basic or objective pressure on person $i$ resulting from the decision of another entity or individual $k$, the decisional influence $U_{i3}$ which arises from the external decision $D_k$ is given by $$U_{i3} = D_k W_{i3} \tag{13}$$

If two individuals are involved in relationship so that $i = 1$ and $k = 2$, then the relationship relative to the decisions each individual is making is described by the coupled equation pair $$D_1 = \text{SIGN}(E_{11}W_{11} + E_{12}W_{12} + D_2W_{13}) \tag{14}$$

$$D_2 = \text{SIGN}(E_{21}W_{21} + E_{22}W_{22} + D_1W_{23}) \tag{15}$$

Generalizations of the equations may readily be made so as to describe other or more complex decision-making situations or interpersonal relationship situations. See as a starting point, for instance, situations described in the above-cited patent applications of the present inventor.

EMOTIONS

Emotional Tension (T)

When an individual $i$ is subject to conflicting decisional influences $U_{ij}$, emotional conflict, tension, anxiety, or discomfort is felt. When opposing influences are nearly equal, the individual experiences difficulty in making a decision, and emotional tension is at a maximum. Emotional tension according to general experience seems to either be zero or have some magnitude. If a decision is being made and all of the decisional influences are for a decision A, and then even a very small factor in favor of the decision not-A creeps in, tension is felt. These considerations motivate the concept of emotional tension as being proportional to the magnitude of the decisional influence or influences that do not prevail in the decision outcome. In mathematical form tension T is given by $T_i \propto$ LESSER (Summation of the magnitudes of the positive $U_{ij}$ and the Summation of the magnitudes of the negative $U_{ij}$). (16)

in short form, $$T_i \propto \text{LESSER}(\sum_j (U_{ij}+), \sum_j |U_{ij}-|) \tag{17}$$

Feelings (Ḃ)

Another emotion which is a common experience of daily life is that of feeling "good" or "bad", "big", "small", "able", "weak", "strong", "elated", or "depressed". This variable can be positive, negative or zero depending upon how an individual feels since good and bad feelings feel opposite. Even when one has been feeling good, one can start to feel bad at the peak of "emotional position" so the bad-good feelings variable appears to be best described as the time derivative of how "big" one feels. Thus, if emotional position or "bigness" be denoted by B, the emotional bad-good feelings variable appears to be properly denoted by the time derivative of B, namely dB/dt or Ḃ. This bad-good feelings variable Ḃ is somewhat similar to utility or integrity as those concepts are employed in economics and mathematical psychology. Utility, like Ḃ, is a variable which the individual desires to make as positive as possible, and this consideration has led to consideration of optimization theory in connection with mathematical analyses in the aforementioned fields.

Ḃ may be further defined and measured by considering the following matters: Ḃ can be positive, negative or zero. If one's personal desire is thwarted it is negative. If one doesn't desire something very strongly, the satisfaction of that desire results in positive Ḃ but does not yield a very large magnitude of Ḃ. These considerations motivate defining the bad-good feelings of individual $i$ as $$\dot{B}_i \propto U_{ii} D_i \tag{18}$$

In words, this formula (18) expresses the concept that personal desire and personal decisions interact to yield feelings. Put another way, Ḃ measures how we feel about ourselves, or how we like ourselves. When the personal desire and personal decision are of the same polarity or sign, then feelings are positive, or "good", but when they are of opposite sign, then feelings are negative, or "bad". Emotional position B is the time integral of $U_{ii}D_i$.

Mood

There is further consideration in connection with feelings that goes beyond the scope of the definition of Ḃ. It is also a fact of common experience that one feels worse when there are conflicting desires relative to a given decision. Furthermore, the conflict, such as a conflict of conscience, often arises because of internalization of norms and other outside pressures on the individual. Therefore, if a $U_{ij}$ is internalized it should be taken into account in a consideration of emotional concepts of feelings. Accordingly, a mood variable for individual $i$ is given by $$M_i \propto \left[ U_{ii} + \sum_{j \geq 2} U_{ij}(\text{if internalized}) \right] D_i \qquad (19)$$

A simple example will help to motivate the definition. A person desires to do and in fact does a socially frowned upon thing. If the social pressure $U_{i2}$ is not internalized, and no other influence besides $U_{ii}$ is present, the person does the thing and feels good ($\dot{B}>0$), and he doesn't care what society says. But if social pressure is internalized, some of the joy is taken out of the doing. In the formula, $U_{i2}$ will be of opposite sign to $U_{ii}$ resulting in lowered mood $M_i$.

Guilt-Pride

The added component $$\left[ \sum_{j \geq 2} U_{ij}(\text{if internalized}) \right] D_i$$

found in formula (19) leads one to consider what its character is. The degree to which one's own decisions are consistent with social and other decisional influence pressures due to specific persons and other factors relates to pride, and inconsistency therewith results in guilt or shame feelings. Thus, there is an emotional variable distinct from feelings $\dot{B}$ which can be positive, negative, or zero. This variable is denoted P and is defined such that $$P_i = \begin{cases} \text{positive, if prideful or conforming} \\ \quad \text{feelings occur} \\ \text{zero, if non personal-desire} \\ \quad \text{influences are absent or uninternalized} \\ \text{negative, if guilt or shame feelings} \\ \quad \text{occur} \end{cases} \qquad (20)$$

For an individual $i$ the level of guilt-pride feeling $P_i$ is related to influences and decisions by $$P_i \propto \left[ \sum_{j \geq 2} U_{ij}(\text{if internalized}) \right] D_i \qquad (21)$$

Notice that mood is equal to the sum of feelings and guilt-pride:

$$M_i = \dot{B}_i + P_i \qquad (22)$$

Specific components of guilt and pride can be isolated by multiplying specific $U_{ij}$ with $D_i$. Guilt and pride can be indicated on the same or separate meters in simulation.

Like-Dislike

While $\dot{B}$ is the variable which describes how we feel about ourselves, we also have feelings about other individuals, entities or things. Like and Dislike resemble positive and negative points or poles of a spectrum and so one is led to define a variable $$L = \begin{cases} \text{Positive, if like} \\ \text{zero, if indifference or if no} \\ \quad \text{object for feeling is present} \\ \text{Negative, if dislike} \end{cases} \qquad (23)$$

Like-dislike depends upon personal desire $U_{ilx}$ but is related to an object Q, where $$Q = \begin{cases} \text{Positive, if desired} \\ \text{Zero, if absent} \\ \text{Negative, if not desired} \end{cases} \qquad (24)$$

So $L_{iq} \propto U_{il} Q$ \qquad (25)

When Q is the decision of another person $k$, the like-dislike relationship of person 1 relative to $k$ becomes $$L_{ik} \propto U_{il} D_k \qquad (26)$$

where $D_k$ is taken to be zero if person $k$ is absent. Thus, in a relationship between a person 1 and a person 2, $$L_{12} \propto U_{11} D_2 \qquad (27)$$

is the like or dislike of person 2 by or in the eyes of person 1 and $$L_{21} \propto U_{21} D_1 \qquad (28)$$

is the like or dislike of person 1 by or in the eyes of person 2.

Notice that like-dislike is proportional to the relevant personal desire compared with the object Q or decision of another, $D_k$. Thus, if a desire is thwarted by another, we feel dislike, annoyance, or the like, for the other in proportion to the desire, and if it is satisfied, we feel liking of the other in similar proportion. If the other person is absent to experience or memory, like or dislike does not occur relative to that person, entity, or thing. Anger, hatred, fear, disgust, antipathy, irritation, annoyance and the like can relate to "dislike" as herein considered, while love, confidence, satisfaction, sympathy and the like can relate to "like" as herein considered.

Disagreement-Agreement

The state of agreement or disagreement between two people amounts to a comparison of their decisions $D_i$ and $D_k$. If the state of agreement be denoted A then $$A = D_i D_k \qquad (29)$$

where $$A = \begin{cases} +1 \text{ if } D_i \text{ and } D_k \text{ are of same sign} \\ 0 \text{ if either individual is absent} \\ -1 \text{ if } D_i \text{ and } D_k \text{ differ in sign} \end{cases} \qquad (30)$$

DETAILED DESCRIPTION OF THE DRAWING

FIG. 1 pictorially shows a simulator according to the invention of two individuals in man-woman relationship. Plug 17 is connected to a power source and power switch 16 is turned on, energizing electronic circuits inside cabiner 15. A replaceable or overlayable panel 1 provides interpretations in terms of a sexual decision of each partner for the corresponding adjustment dials, switches, meters, and decision indicators.

These include adjustment dial 7, Personal Desire; 5, Attention to Own Desire or weight; 8, Social Expectations; 6, Compliance with Society or weight; and 4, Emotional Independence from Woman or weight. Also, there are switches 9, Influence of Man, and 25, Internalization of Social Expectations; meters 20, Tension; 21, Dislike-Like; 23, Feelings: Bad-Good; and 24, Guilt-Pride; and decision indicating lamp assemblies 2 and 3 for the Man's decision to Avoid or Participate respectively. The corresponding items-- adjustment dials 7',5',8',6',4'; switches 9' and 25'; meters 20',21',23', and 24'; and decision indicating lamp assemblies 2' and 3' serve the corresponding functions for the simulator of the woman.

Decisions of the man-simulator and woman-simulator made available at decision ports 10 and 10' are communicated via wires 12 and 12' to sense ports 11' and 11 of the woman and man-simulators respectively. Disagreements, when they occur in simulation, are signalled on indicator lamp assembly 22. Overlay sheet 14 having knob holes 19 may be fastened with clips 13 and 13' on the panel 1 so that the situation or decision being simulated may be changed or interchangeably indicated--a decision relating to the woman's home or career plans being illustratively suggested for an alternative situation simulation.

Man's Emotions

Considering now the simulated sexual decision illustrated in FIG. 1 it is seen that the man's compliance 6 with social expectations 8 and the influence 4 of the woman outweight the man's personal desire 7 as mediated by his attention to own desire 5 so that the man participates in sexual relationship as indicated by lamp assembly 3. Since his activity denoted by $D_1 = 1$ corresponds with a decisional influence, due to social expectations, say $U_{12} = +1$ due to settings of dials 8 and 6, he feels pride $P_1 = U_{12}D_1 = \times 1 = 1$ as indicated on Guilt-Pride meter 24. Guilt-Pride is nonzero since switch 25 is set to show that the man has internalized social expectations; otherwise it would be zero.

Although the man feels pride, he feels bad, because what he is doing $D_1=1$, conflicts with his personal desire decisional influence (due to settings of dials 7 and 5) $U_{11} = -3$. Thus, his feelings about himself are $B_1 = U_{11}D_1 = -3 \times 1 = -3$ as shown on meter 23, feelings being bad.

Because the woman's decision to participate, $D_2=1$, on lamp 3', is in part responsible for thwarting the man's personal inclination to avoid, he, perhaps secretly, dislikes her. This circumstance corresponds to $L_1 = U_{11}D_2 = -3 \times 1 = -3$, as shown on Dislike-Like meter 21.

The conflicting decisional influences on the man due to personal desire, social expectations, and the woman's decision produce emotional tension. Personal desire decisional influence $U_{11} = -3$, social expectation decisional influence $U_{12} = +1$, and influence due to woman's decision (due to emotional independence on dial 4 being very low) is, say, $U_{13} = +6$. The summation of negative influences is $\Sigma U_{1j}- = -3$, and the summation of the positive influences is $\Sigma U_{1j}+ = 6+ = 7$. Tension T = LESSER(magnitude of $\Sigma+$ and $\Sigma-$)= LESSER(7,3) = 3 as shown on meter 20.

Woman's Emotions

Since the woman's personal desire 7', social expectations upon her 8', and the man's decision 3 all operate (Switch 9 being set to Agreeable) to influence her toward participation, the resulting decision to participate is displayed by lamp assembly 3'. Since her activity of participation $D_2 = 1$ is in accord with social expectations, then with decisional influence $U_{22} = +2$ due to settings of social expectations dial 8' and Compliance with Society dial 6', she feels pride $P_2 = U_{22}D_2 = +2 \times 1 = +2$ as indicated on Guilt-Pride meter 24'.

Not only does the woman feel pride; she also feels good since her decision accords with her personal desire. However, this emotion is quite attenuated due to her low attention to own desire 5' resulting in personal desire decisional influence $U_{21} = +1$ and $B_2 = U_{21}D_2 = +1 \times 1 = +1$, as shown on meter 23', feelings being good.

Because the man gives no outward sign of his conflicting feelings in this hypothetical example, the woman is unaware of anything but his responsive participation, $D_1=1$. This satisfies her personal desire and she likes him for it. This circumstance corresponds to $L_{21} = U_{21}D_1 = +1 \times 1 = +1$, an emotion of liking on the Like-Dislike meter 21'.

No conflicting decisional influences impinge upon the woman, unlike the man in this illustration, because all of the decisional influences are positive, that is, in favor of a decision to participate. Consequently, tension T = LESSER(Magnitude of $\Sigma+$, Zero) = Zero, as shown on tension meter 20'.

Since the decisions of the man and woman to participate are in accord, there is no disagreement and consequently lamp assembly 22 is dark.

It should be apparent that the dial settings given in the example are but one example of numerous dial settings for other situational examples. The dials and circuitry permit operation so that the decisions indicated and the emotional meter readings are always in accord with the dial and switch settings and in conformity with the theory example above-disclosed. In this manner, operation of the invention is rendered a fascinating and often surprising experience for the user, as for instance when dial 7' is rotated in the direction of arrow 18.

Figure 2A:
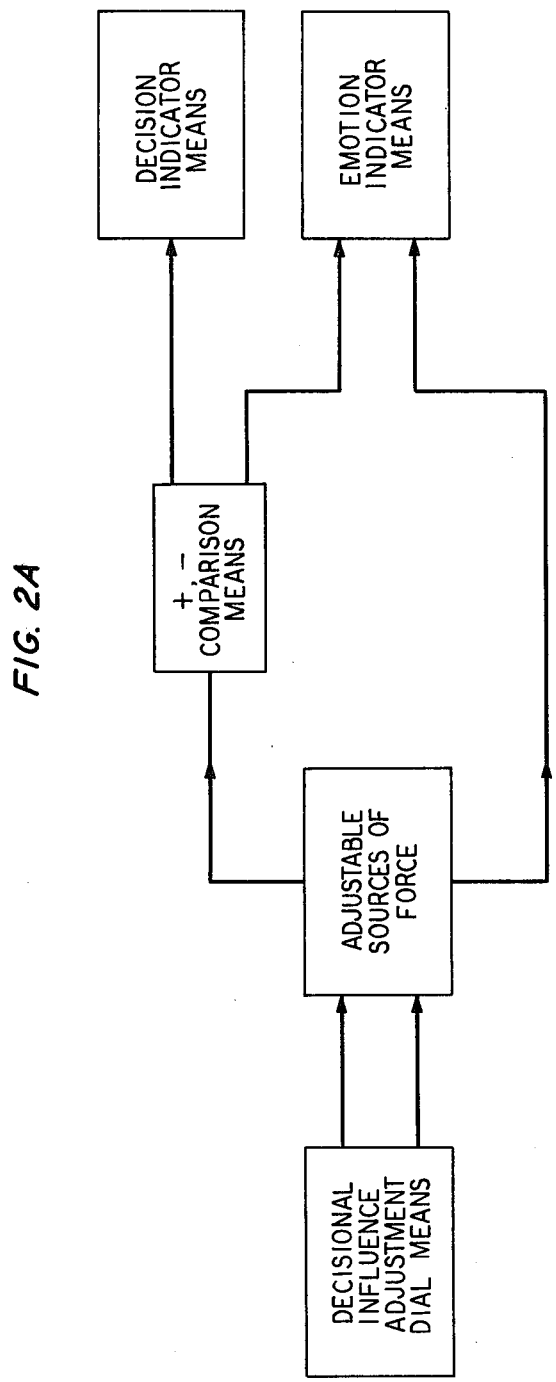
FIG. 2A is a block diagram of apparatus of the invention such as that of the embodiment of FIG. 1, the block diagram also serving to illustrate the method of the invention.

FIG. 2A is a block diagram useful in clarifying the broader aspects of the apparatus and method of the present invention, as well as explaining the complexities of circuits and other apparatus of the preferred embodiments prior to going into details in succeeding figures of the drawing. In the invention emotions are recognized as being related to decisional influences of various types. Qualitative types or polarities of decisional influences as tending to exert pressures to cross-purposes are described for purposes of discussing the present invention as being positive or negative. Decisional influences may be exerted toward merely alternative decisional outcomes, logically complementary outcomes, decisional outcomes which are opposite in some sense, or outcomes characterizable in other ways.

In one aspect of the invention a plurality of sources of respective physical forces are provided, at least one of the sources being substantially continuously adjustable in level. A force level has magnitude and can have positive or negative sign so that the forces are relatable to the decisional influences just mentioned. The forces can be electrical voltage, electrical current, fluidic pressure or flow, mechanical force or motion, acoustic intensity, frequency, optical intensity, heat or temperature, chemical influences, or other features of physical systems which are included under the heading of physical force as a term of convenience. Means are provided for comparing the forces so as to determine whether a combined total, such as a linear combination or a sum total or other combined total, of at least two of the decisional influences referenceable to the forces is greater or less than a threshold value.

When the threshold value is zero, the comparison determines whether the combined total is positive or negative in character. A mathematically equivalent statement can be that when the threshold value is zero, the comparison also determines which of a combined total of the magnitudes of the positive polarity decisional influence levels and a combined total of the magnitudes of the negative polarity decisional influence levels is the lesser or the greater in magnitude. There exist a variety of other mathematically equivalent statements as well and any comparing means accomplishing such a mathematically equivalent operation can be useful in some embodiment of the present invention.

The invention then provides means of indicating one or more simulated emotions each of which can have levels which have magnitude and can have polarity, by measuring as an emotion at least on of the physical forces including the force from the substantially continuously adjustable force source in a manner dependent on the determination provided by the comparing device.

In another aspect of the invention as a type of decisionmaking simulation apparatus which has means for indicating and adjustably varying the levels of the decisional influences and means for indicating one of a plurality of alternative decisions, the invention provides physical system means of any suitable type for (A) causing the decision indicator means to indicate a first decision when a combined total of at least some of the variable levels is above a threshold level and otherwise to indicate a different decision and (B) deriving and indicating at least one simulated emotional level dependent upon at least one of the decisional influence levels and upon whether the combined total is above or below the threshold.

Still other aspects of the invention focus upon it as not only apparatus for performing a process, method, or technique, but also as the process, method, or technique itself. These aspects involve (A) steps of generating analogs, which might be analog force levels or arrays of forces coded in some manner to relate to the decisional influences, (B) comparing (as to determine a positive or negative character of a combined total, or comparing to a threshold, or finding a lesser or greater quantity, or some other comparing step), and (C) producing an emotional analog and indicating it to have a magnitude and sign depending on the generated analog forces and comparing step outcome.

Accordingly, FIG. 2A shows the adjustable source of force, the +,− comparing means and emotion indicator means of the invention. Likewise, it shows a decisional influence adjustment means including adjustment dial means which is linked with decision indicator means by a physical system featuring emotion indicator means utilizing force analogs and comparison means. The force sources can be associated with one or more simulated individuals for indicating solitary psychological phenomena or social psychological phenomena of interpersonal relationships of one-way, reciprocal, and other type.

Comparison of FIG. 2A with the more detailed diagrams, pictorial representations and descriptions of the invention will help to illuminate the invention both in its broad scope and principles and in its remarkable preferred embodiments set forth herein.

Figure 2B:
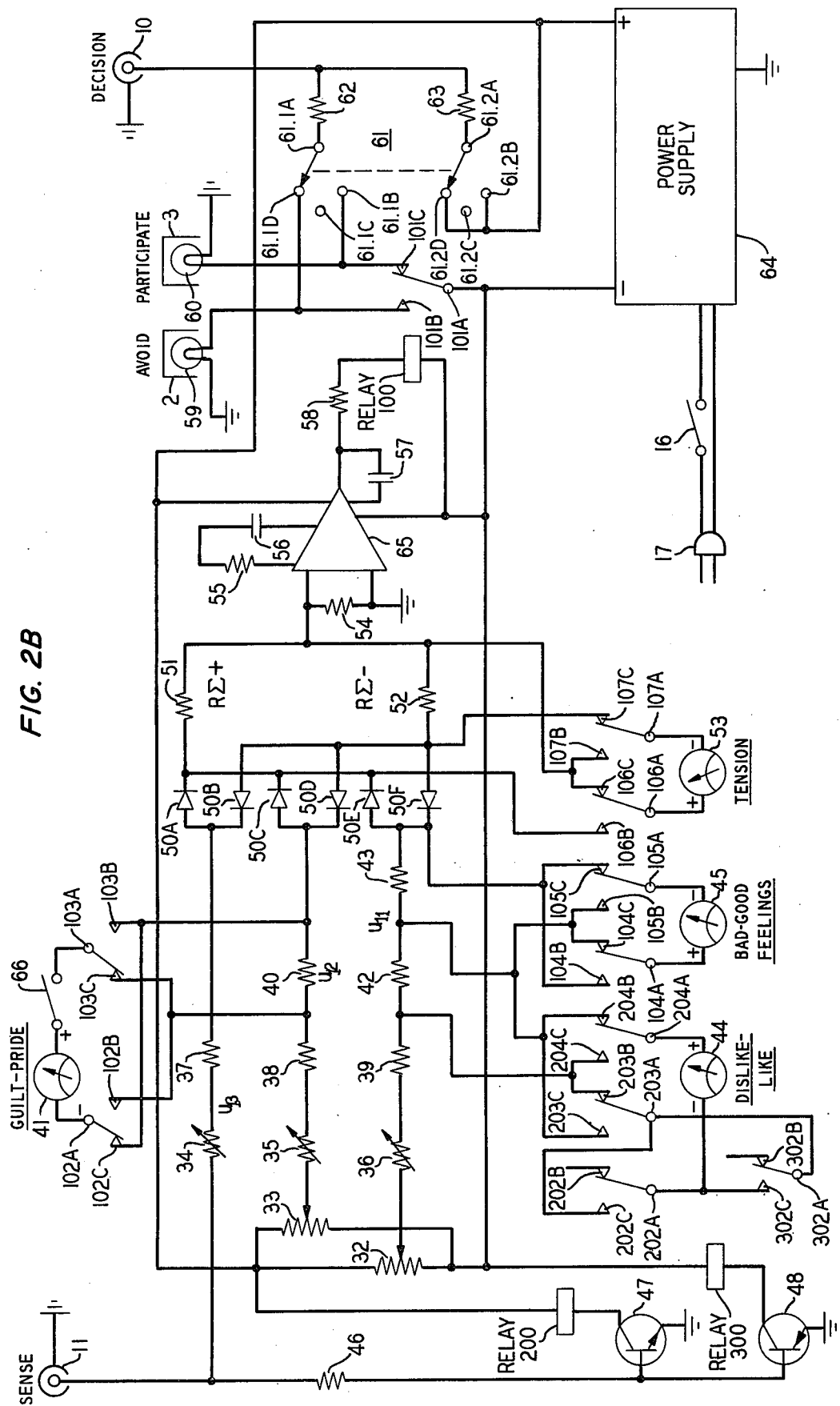
FIG. 2B is a schematic diagram of an electronic circuit for use in the simulator apparatus of FIG. 1 in accordance with the block diagram of FIG. 2A. It will be noted that the circuit shown is duplicated for the number of individuals simulated. Since the apparatus of FIG. 1 involves distinct simulators for two simulated individuals, two of the circuits of FIG. 2B are used in the apparatus of FIG. 1.

FIG. 2B illustrates relative to one such preferred embodiment an electronic circuit physical system which is suitable for inclusion in cabinet 15 of FIG. 1. Power plug 17, power switch 16 and dual-polarity power supply 64 are included in the power circuitry for the simulator. It should be understood that FIG. 2B shows only the simulator circuitry for the man-simulator and that the circuitry for the woman-simulator is identical with the circuit for the man-simulator and fed from the common power supply 64, all woman-simulator component numerals primed, not shown.

Potentiometer 32 attached to personal desire decisional influence level adjustment dial 7 is connected between the positive and negative sides of power supply 64 such that it acts as a continuously adjustable electrical force source such that there appears a voltage $V_{11}$ on the wiper of potentiometer 32 which is analogous to the personal desire basic variable $E_{11}$ of the theory example hereinabove. The wiper of potentiometer 32 is connected to Attention to Own Desire variable resistor 36 which is attached to adjustment dial 5. Isolation resistor 39 and variable attenuation resistor 36 constitute most of the resistance between potentiometer 32 wiper and ground such that their series connection has conductance $G_{11}$ which is analogous to weight variable $W_{11}$ in the theory example. The current in the path through the resistor 39 is essentially $I_{11} = V_{11}G_{11}$ which is analogous to the personal desire decisional influence $U_{11} = E_{11}W_{11}$.

Potentiometer 33 attached to Social Expectations decisional influence level adjustment dial 8 is connected between the positive and negative sides of power supply 64 such that potentiometer 33 acts as a second continuously adjustable electrical force source such that there appears a voltage $V_{12}$ on the wiper of potentiometer 33 which is analogous to the social pressure basic variable $E_{12}$ in the theory example. The wiper of potentiometer 33 is connected to Compliance with Society variable resistor 35 which is attached to adjustment dial 6. Isolation resistor 38 and variable resistor 35 constitute most of the resistance between potentiometer 33 wiper and ground such that their series connection has conductance $G_{12}$ which is analogous to weight variable $W_{12}$ in the theory example. The current in the path through the resistor 38 is essentially $I_{12} = V_{12}G_{12}$, which is analogous to the social pressure decisional influence $U_{12} = E_{12}W_{12}$. The electrical influence currents just mentioned may be considered as physical forces in the sense of the term "force" used herein.

Sense terminal 11 of the man-simulator receives a decision physical force or voltage $V_2$ transmitted from the woman-simulator decision terminal 10'. The woman-simulator decision voltage $V_2$ is suitably a positive voltage corresponding to Participate, or an equal magnitude and opposite sign voltage corresponding to Avoid, or zero corresponding to absence of the woman from the relationship or from consideration. Thus, the woman decision voltage $V_2$ is analogous to the woman decision variable $D_2$. The voltage $V_2$ is fed to variable resistor 34 attached to adjustment dial 4, Emotional Independence from Woman, and connected to isolation resistor 37, the two resistors 34 and 37 constituting most of the resistance in their path from sense terminal 11 to ground. The conductance of the series resistors 34 and 37 is $G_{13}$. Thus, the current flowing through resistor 37 is $I_{13} = V_2 G_{13}$, which is analogous to a decisional influence due to a romantic partner $U_{13} = D_2 W_{13}$.

Currents $I_{11}, I_{12}$, and $I_{13}$ make their way essentially unaffected through emotion-measuring circuits to be more fully described hereinbelow and eventually arrive for comparison at the input of comparison means illustratively including operational amplifier 65 or any suitable alternative threshold level detector means. Resistor 55, Capacitor 56 and Capacitor 57 are compensating components to limit the bandpass of the operational amplifier 65 to essentially direct current, less than 30 Hertz being quite suitable. The operational amplifier 65 is powered from both sides of power supply 64 and provides an output voltage which is sufficient to actuate selector relay 100 through current limiting resistor 58 providing the sum of $I_{11}$, $I_{12}$, and $I_{13}$ is greater than zero (positive in character) and not actuating selector relay 100 if said sum is less than zero (negative in character). When relay 100 is actuated, or closed (contact assembly armatures A connected to contacts C), the negative side of power supply 64 is connected via armature 101A to relay contact 101C so that Participate lamp 60 lights up in lamp assembly 3 of FIG. 1. If relay 100 is not actuated (contact assembly armatures A connected to contacts B), the negative voltage passes to relay contact 101B to light lamp 59 in lamp assembly 2 (Avoid).

It will be noted that panel 1 of FIG. 1 is marked and the potentiometers and variable resistors wired so that, for example, positive voltages or currents correspond to a decisional influence to Participate and negative voltages or currents correspond to decisional influence to Avoid. High Attention to Own Desire on dial 5 and High Compliance with Society correspond to low resistance 36 and 35 settings, but High Emotional Independence from Woman corresponds to a high resistance setting of variable resistor 34.

Operational amplifier 65 is wired so that a positive combined total input voltage or current produces a positive voltage on the coil or relay 100 relative to the negative side of the power supply so that selecting relay 100 will be actuated. Then when selecting relay 100 is actuated a positive voltage $V_1$ is derived analogous to decision variable $D_1$ and appears at the decision port 10 of the man-simulator due to the voltage divider action of a network consisting of resistors 63 and 62 connected with switch 61 having switch handle 9 of FIG. 1.

The positive side of power suppy 64 is connected via contact 61.2D (D contact of second section of double pole triple throw (DP3T) polarity dependence reversing switch 61) to rotor 61.2A to resistor 63 which in turn is connected to one end of resistor 62 and decision port 10. Resistor 62 is connected via rotor 61.1A to contact 61.1D through darkened or unlit lamp 59 to ground, completing the voltage divider. Thus, when switch handle 9 of FIG. 1 is set to Agreeable so that switch 61 is set as shown in FIG. 2B, a positive voltage appears and is made available at decision port 10 for communication or transmission to the woman-simulator when Participate lamp 60 in lamp assembly 3 is lit. On the other hand, when switch handle 9 is set to Contrary so that rotors 61.1A and 61.2A are connected to contacts 61.1B and 61.2B respectively, then when Participate lamp 60 is lit the resistors 62 and 63 provide a negative voltage of equal magnitude to the positive voltage, to decision terminal 10.

The required resistance ratio of resistors 62 and 63 in such a divider is $$\frac{R_{62}}{R_{63}} = \frac{-V-}{2V+} \tag{31}$$

For example, if a conventional dual polarity power supply for which $V+ = -V-$ is used, $R_{62} = \frac{1}{2} R_{63}$ is needed to provide a decision output voltage $V_1$ of dual polarity type, the polarities corresponding to decision alternatives and being dependent on the determination of the comparison or threshold detector means.

When switch 61 is set to its central position by setting switch handle 9 to None, so that rotors 61.1A and 61.2A are connected to an "off" position or to unused contacts 61.1C and 61.2C respectively, then the decision output force or voltage $V_1$ is interrupted and decision port 10 floats electrically.

Resistors 62 and 63 are preferably chosen such that the output impedance presented by them is small compared to the input impedance seen at terminal 11 so that one simulator can provide influence to one or more other simulators like the distinct decisionmaking simulator for the woman in FIG. 1. The output impedance at decision port 10 is $$R_{out} = \frac{R_{62} R_{63}}{R_{62} + R_{63}} \tag{32}$$

and the input impedance at sense port 11 is approximately $$R_{in} = \frac{R_{46}(R_{34} + R_{37})}{R_{46} + R_{34} + R_{37}} \tag{33}$$

The design of the woman simulator is suitably but not necessarily identical to that of the man-simulator circuit disclosed and described hereinabove.

Next we turn our attention to the circuits for derivation, measurement, and indication of simulated emotional levels.

Meter 45 of FIG. 2B for Bad-Good Feelings corresponds to the meter numbered 23 in FIG. 1. This meter measures the emotion $\dot{B}$ according to the previously given formula $\dot{B} \propto U_{11} D_1$. For this purpose the single current $I_{11}$, or equivalently a portion thereof, is measured in a manner reversibly modifiable in polarity by the comparison determination made by the threshold detector 65, the comparison being taken into account by an extra set of contacts 104 and 105 on selector relay 100. Thus, when $I_{11}$ is positive and selector relay 100 is actuated, corresponding to a positive character of combined input influence total and positive $V_1$ and $D_1$, then positive current proportional to $I_{11}$ flows around shunt resistor 43 to relay contact 104C of relay 100 into relay armature 104A to the positive side of meter 45 and out the negative side of meter 45 to relay armature 105A into relay contact 105C and back to the opposite side of shunt resistor 43. Meter 45 then reads positive or "good" feelings.

However, if the effect of the personal desire decisional influence current $I_{11}$ is overwhelmed by contrary currents $I_{12}$ and $I_{13}$, producing a negative character of combined input influence total, then relay 100 is not actuated and the result is that current flows around shunt resistor 43 to relay contact 105B of relay 100 to relay armature 105A into the negative side of the meter 45 and out to positive side of meter 45 to relay armature 104A to contact 104B to the other side of shunt 43. Then meter 45 reads negative or bad feelings in proportion to the strength of personal desire decisional influence analog current $I_{11}$.

Similarly, it can be readily shown that if $I_{11}$ is negative and the relay 100 is not actuated, meaning that the combined total character and decision variable is negative, then the meter 45 reads positive feelings B, and if the $I_{11}$ current is negative and the relay is actuated then the meter 45 reads negative feelings. In this manner a form of the invention for measuring a simulated emotion is constructed by measuring $I_{11}$ in a manner dependent on whether its polarity is the same as or opposite to a combined total of the currents to comparing detector 65 connected to selector relay 100.

In a quite similar way, the Guilt-Pride meter 41 is wired into the circuit of FIG. 2B so that the electrical analog of the formula $P_1 = U_{12}$ (if internalized)$D_1$ is produced. In this way means for indicating levels of an emotion related to social estimation perceived by oneself is obtained. If switch handle 25 of FIG. 1 of switch 66 of FIG. 2B is set to Social Expectations—Externalized, then switch 66 is open and there is no reading of Guilt or Pride on meter 41 except zero because the meter is disabled by the switch 66. However, if switch handle 25 of switch 66 is set to Social Expectations—Internalized, then switch 66 is closed and meter 41, now enabled, reads a magnitude proportional to social expectations or pressure current $I_{12}$ with sign controlled partly by said current $I_{12}$ and partly by the positive or negative character of the combined total controlling the state of selector relay 100 due to the meter connections to the relay.

For example, if social expectations current $I_{12}$ is positive and relay 100 is actuated corresponding to a decision variable $D_1 = +1$ (conformity with social expectations; combined total of same character as $I_{12}$ decisional influence force), then current flows around shunt resistor 40 to relay contact 103C of relay 100 to relay armature 103A to the positive side of meter 41 and out the negative side of meter 41 to relay armature 102A to relay contact 102C to the opposite side of shunt resistor 40. Thus, if the relay is actuated, meter 41 reads a positive value corresponding to an amount of Pride proportional to the social expectations decisional influence, and positive because the social expectations and combined total of decisional influences have the same sign. If on the other hand the relay is not actuated (nonconformity with social expedations), then meter 41 is polarity reversed by the relay contacts 102 and 103 and reads a corresponding negative emotion of shame or guilt because the social expectations and combined total of decisional influences are opposite in their positive or negative character.

Turning to the Like-Dislike meter 44 of FIG. 2B corresponding to the meter numbered 21 in FIG. 1, we observe that this meter is wired in shunt with shunt resistor 42 so as to at least sometimes read proportional to personal desire decisional influence current $i_{11}$ which is analogous to $U_{11}$. However, instead of being connected with relay 100, meter 44 for Like-Dislike is connected with relays 200 and 300 so as to read analogous to the formula $L_{12} \propto U_{11}D_2$. Here, then, it is the relays 200 and 300 which when the woman-simulator is connected to sense port 11 coact with the comparison detector 65' in the woman-simulator and force sources therein in comporting with the scheme of the invention as indicated in FIG. 2A.

If there is no voltage available at sense port 11, meaning that there is no individual present to the man in simulation, then non current will flow in resistor 46 to turn either transistor 47 or transistor 48 on and actuate either relay 200 or relay 300. This means that there will be no conductive path through either disabling-enabling SPDT assembly 202, including armature 202A, and contacts 202B and 202C of relay 200, or through disabling-enabling SPDT assembly 302, including armature 302A and contacts 302B and 302C of relay 300 which are wired in parallel with each other and in series with meter 44. The result is that unless there is a decisional influence voltage at sense port 11 there will be no reading of Dislike or Like on meter 44, save zero, since the meter is disabled; and according to the theory example there is no like or dislike in the absence of an object, or present individual, or memory to interact with personal desire.

However, when a decisional influence voltage is present at sense port 11, then one of the relays 200 or 300 is actuated and meter 44 is connected to SPDT assemblies 203 and 204 of relay 200 to take the sign information of the combined influence total in the woman-simulator into account. For example, if the man in simulation wants to participate ($I_{11}$ positive) and the action of the woman in simulation is avoidance ($V_2$ negative at sense port 11), then positive current flows around shunt resistor 42 from resistor 39 to contact 203B to armature 203A of relay 200 to armature 302A of relay 300 to contact 302C (relay 300 actuated due to negative $V_2$ sending negative current through resistor 46 to transistor 48 base to emitter to ground) to the negative side of meter 44 to the positive side of meter 44 to relay armature 204A of relay 200 to contact 204B to the other side of shunt resistor 42. The result is that meter 44 reads negative, indicating the dislike of the man in simulation for the avoidance of the woman in simulation.

If the woman decides to participate $V_2$ becomes positive at sense port 11, actuating relay 200, which reverses in polarity the reading of meter 44, so that a reading of Like is displayed. Again the invention involves a comparison of the sign of $I_{11}$ with the positive or negative character of a combined total of influences, liking if same, disliking if opposite. It can be seen that emotions in interpersonal relationships can change abruptly as represented by the simulation apparatus of the invention.

Tension meter 53 of FIG. 2B corresponding to meter 20 of FIG. 1 displays emotional tension, or nervous tension, or degree of conflict between influences and values, or uncomfortableness, or the like. It will be recalled that according to the above-disclosed theory example, Tension is proportional to the lesser of the magnitudes of a subtotal sum of the positive decisional influences and a subtotal sum of the negative decisional influences. In FIG. 2B a circuit for deriving this quantity is provided in the form of reverse- and forward-connected diodes 50A–50F, combining or summation resistors 51 and 52 and summation selector relay 100 having SPDT contact assemblies 106 and 107. Currents $I_{11}$, $I_{12}$, and $I_{13}$ corresponding to decisional influences $U_{11}$, $U_{12}$, and $U_{13}$, are routed according to polarity so that if positive they flow through summation resistor 51 and if negative they flow through summation resistor 52, by the action of the diode network, two diodes being provided for each line from each isolation resistor 37, 38, and 39.

For example, if personal desire decisional influence current $i_{11}$ is positive, then $I_{11}$ flows from shunt resistor 43 through forward-connected diode 50E to resistor 51. Reverse-connected diode 50F is reverse-biased in this condition and presents essentially an open circuit between shunt resistor 43 and summation resistor 52. On the other hand, if $I_{11}$ is negative, diode 50F is forward-biased and $I_{11}$ flows in summation resistor 52. Then diode 50E is reverse-biased and summation resistor 51 is isolated from current $I_{11}$.

The result of the routing in the diode network is that the voltage drop measured from relay contact 106B of relay 100 to the ungrounded input of operational amplifier 65 across summation resistor 51 is proportional to the summation of the positive decisional influences, and the voltage drop from relay contact 107C to the ungrounded input across resistor 52 is proportional to the summation of the negative decisional influences. In other words, the resistors 51 and 52 provide positive and negative polarity resistive paths respectively. Resistors 51 and 52 are preferably equal in electrical resistance to a degree of precision of less than 5% difference in this circuit so that the same current produces the same voltage, if meter 53 has substantial resistance of its own. However the equality of the resistances is relatively unimportant if the meter 53 resistance is considerably smaller than either summation resistance.

The next step in the circuit is to select a tension quantity proportional to the lesser of the magnitudes and display that magnitude on tension meter 53. It is to be emphasized that meter 53 is not a positive-and-negative reading galvanometer as are meters 41, 44, and 45, but rather is a simple positive reading meter. Meter 53 is permitted to read tension in accordance with the following principle: the sum of currents which is lesser in magnitude will correspond to decisional influences which do not prevail in the final decision reached. In other words, when the combined total of all of the decisional influences is determined to be positive in character by the comparing detector 65, then the subtotal of negative levels must be lesser in magnitude; and when the combined total of all of the decisional influences is determined to be negative in character, then the subtotal of positive levels must be lesser in magnitude. The nature of the final decision, hence the state of selector relay 100, to which the output of comparing detector 65 is connected, tells which sign of decisional influence is lesser and did not prevail.

The subtotal summation resistors 51 and 52 are wired to SPDT contact assemblies 106 and 107 of relay 100 and thence to meter 53. For instance, if relay 100 is actuated, meaning that the combined influence total is positive in character, then the magnitude of the sum of the negative influence currents must be lesser in magnitude than the sum of the magnitudes of the positive influence currents. When relay 100 is actuated, armatures 106A and 107A are connected to relay contacts 106C and 107C as shown in FIG. 2B so that meter 53 has its positive side connected to the positive (comparison input) side of negative summation resistor 52 and negative side connected to the negative side (diode side) of resistor 52. In this way, the magnitude of the summation of the negative influence currents is read by meter 53. If, on the other hand, relay 100 is not actuated, meaning that the combined influence total is negative in character, the sum of the positive currents must be lesser in magnitude and meter 53 is selectively connected through relay armatures 106A and 107A to contacts 106B and 107B to positive summation resistor 51 in the correct sense to read the positive subtotal magnitude. In this manner the meter 53 and associated circuitry correctly implement the tension formula and indicate a quantity relating the emotional conflict of nervous tension.

In the illustrative embodiment of the invention of FIGS. 1 and 2B the following parameters and component values are suitably employed: Positive supply voltage +9 volts; negative supply voltage −9 volts; R32=R33=10,000 ohms (10K) linear taper; R34=R35=R36=100,000 ohms (100K) linear taper; R37=R"=R39=47,000 ohms (47K); R40=R42=R→=R|=R52=1000 ohms (1K); R54=R58=470 ohms; R46=10,00 ohms (10K); transistors 47 and 48 are NPN and PNP medium beta (30–100) respectively, although alternative other conventional relay drivers are suitable as well. Operational amplifier 65 is a type 709 relay driver differential amplifier of widely available type with gain in the hundreds or thousands having wired thereto a compensation network for gain at or below 30 Hertz such that R55=1500 ohms, capacitor C56=0.02 microfarads, and output compensation capacitor C57=220 picofarads.

When the positive or negative character of the combined total influence changes, the 709 output is driven directly to the positive or negative supply voltage with substantially negligible time spent in the intermediate operating region, thereby allowing the operational amplifier to act as a threshold level detector or comparison means. The 709 pins are wired from output resistor R58 clockwise as follows: 8,1,2, 4,3,6,5,7 (referring to FIG. 2B). Relays 100, 200, and 300 have contacts as shown in FIG. 2B and relay coils rated at suitably 6 to 9 bolts, 500 ohms, 12 milliamperes.

Diodes 50A–50F are forward-connected for 50A, 50C, and 50E and reverse-connected for 50B, 50D, and 50F, all the diodes suitably being about 10,000 (10K) or less in forward resistance at circuit current and 2 megohms or greater in reverse resistance. Meters 41, 44, 45, and 53 are 100 microamperes full scale meters with 1000 ohm coil resistance or less. The meters have polarity reversible relay connections to respective 1000 ohm meter shunt resistors R40, R42, R43, and subtotal summation shunts R51, R52 which provide advantageous electromechanical damping to the meter movements. In the voltage divider output network R62=1000 ohms (1K) and R63=2000 ohms (2K).

This completes the description of a specific preferred electrical embodiment of the present invention for measuring simulated emotional levels. It will be noted that several simulated emotions can be measured simultaneously but that any one or more of the meters can be disconnected if it is desired to measure any subset of the emotions to the exclusion of the others.

FIG. 3 shows an alternative adjustment means 310 of a type suitable for use in place of the adjustment dials including knobs 7,7',8, and 8', for instance. Instead of an adjustment dial comprising a single knob with panel markings, the panel 1 has adjustment means 310 including adjustment dial 311, 312 and qualitative polarity adjustment switch handle 313 set to choose the decision alternative to which the desisional influence (here "Personal Desire") relates, for instance "Do". Quantitative level adjustment is set by Knob 311 connected to a linear sliding variable resistor or potentiometer, and the decisional influence level is indicated by reference to panel markings 312. The adjustment means 310 indicates a decisional influence level of +4 favor of the decision alternative "Do" in FIG. 3.

FIG. 4 shows a portion of an electric circuit suitable for the employment of the adjustment means 310 of FIG. 3. Knob 311 of FIG. 3 is attached to linear sliding potentiometer 411 of FIG. 4, and switch handle 313 corresponds to schematically indicated switch 413 having ganged DPDT contacts 413A and 413B. Dual polarity power supply 64 is connected to polarity selector switch 413 so that positive voltage is fed to potentiometer 411 if the Personal Desire is for "Do", else negative voltage if Personal Desire is for "Avoid". Attention to Own Desire adjustment dial means such as knob 5 of FIG. 1 is attached to variable resistor 412 which in turn is connected to the wiper of linear sliding potentiometer 411 and isolation resistor 414.

The SPDT switch segment 413B is ganged to 413A so as to selectably deliver positive polarity voltage to summation resistor 51 or negative polarity voltage to summation resistor 52 without need of diode network 50A through 50F of FIG. 2B. The summation current reaches operational amplifier 65 and swamping resistor 54 in the usual manner. A switching network including a plurality of circuits like 413,411,412,414 connected to buss wires 415,416,417, and 418 is suited for accomodating as many decisional influences as are required in the simulator.

In an alternative electrical circuit, eliminating the need of relay contacts 106 and 107 of FIG. 2B in the Tension measuring circuit for meter 53, FIG. 5 shows DC amplifiers 516 and 517 respectively connected to positive and negative summation voltages $V_{\Sigma+}$ and $V_{\Sigma-}$ available between a common point at the junction of resistors 51 and 52 (or ground) and the opposite (diode) sides of resistors 51 and 52, respectively. Each DC amplifier 516,517 may, but need not necessarily, consist of a chopper, AC amplifier and peak detector such as 510,511,512; and 513,514,515 respectively. In this manner low level subtotal summation electrical influence voltages from resistors 51 and 52 are advantageously amplified and their voltages proportional to their magnitudes (absolute values) implicity derived at the peak detector outputs.

The LESSER function is provided by selector circuit 518. A balancing network consisting of resistors 519, 520, and balancing potentiometer 521 having wiper 524 connected to ground is preset so that equal magnitude input voltages $V_{\Sigma+}$ and $V_{\Sigma-}$ to the DC amplifiers 516 and 517 produce equal magnitude output voltages of identical polarity to each other at either end of potentiometer 521. Then when general input voltages are applied, diodes 522 nd 523 select the lesser in magnitude of the output voltages which are still identical in polarity and deliver it to output 525 which in turn is suitably connected to a Tension voltmeter not shown.

The circuit of FIG. 5 is suitably used either with a diode network such as in FIG. 2B or with a switching network as in FIGS. 3 and 4 for providing the subtotal summations.

Figure 6:
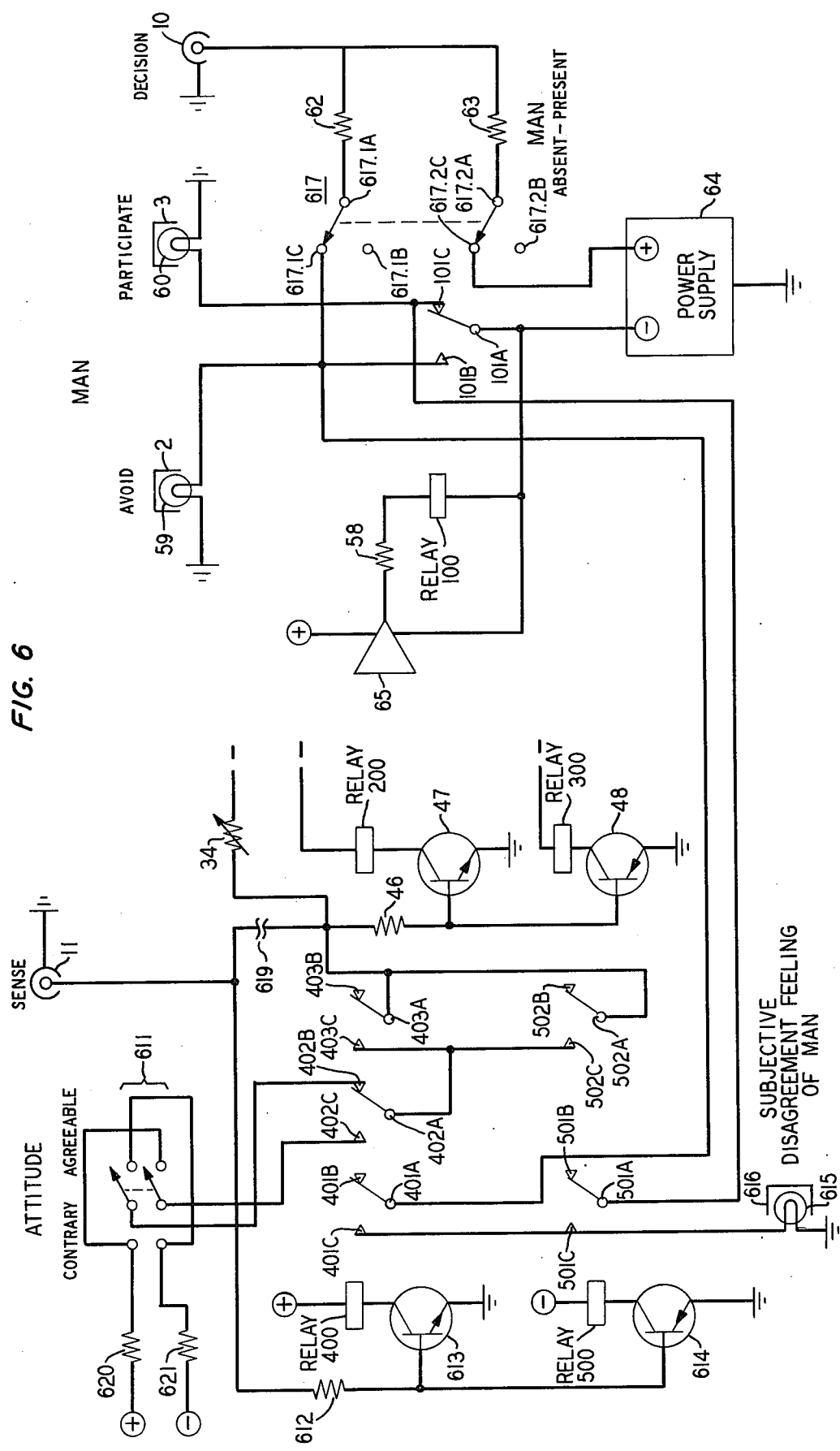
FIG. 6 is a schematic diagram showing how the circuit of FIG. 2B may be modified so that switchable personality perception logic circuitry accounts for an attitude and so that the presence of subjective disagreement feelings is registered.

In another feature of the present invention illustrated in FIG. 6, means are provided for simulating attitudes and subjective disagreement feelings. It will be noted that FIG. 6 represents additions and modifications relative to FIG. 2B, most of the identical circuitry being deleted to clarity except for resistor 46, transistors 47 and 48, relays 100,200, and 300, operational amplifier 65 and resistor 58, and lamps 59 and 60 with lamp assemblies 2 and 3. Sense port 11 is no longer connected to resistor 46 but rather (as suggested by break 619) connected to polarity- and presence-sensing or determining circuitry including resistor 612, transistors 613 and 614 (NPN and PNP respectively) and relays 400 and 500 suitably identical with resistor 46, transistors 47 and 48 and relays 200 and 300 respectively.

The polarity of decisional influence voltage present at Sense Port 11, relatable to a perception of the woman by the man, is passed to resistor 46 either unchanged or reversed in polarity depending on the Contrary or Agreeable Attitude with which the decisional influence voltage is perceived, by the adjustable setting of a DPDT attitude switch 611, suitably having a switch handle and associated panel markings for attitudes.

Since the Contrary-Agreeable attitude setting function is shown in FIG. 6 internal to perceptual processing circuitry in the "front end" of an individual simulator, it becomes unnecessary to employ switch means for Contrary or Agreeable influence such as switch 61 with handle 9 of FIGS. 2B and 1. Therefore, switch 617 at the decision output of the simulator in FIG. 6 is made a two-position interrupting switch for simulating' Man Absent of Present as a replacement for said switch 61. Then the circuitry at the sense input of each simulator of the individual acts as sensory input processing logic means or personality perception logic means for utilizing or perceptually processing the sensed physical force influences which help to influence the emotional indications and result in the indicated decisions.

For example, if the Attitude switch 611 is set for Agreeable, Trusting, or the like, then the voltage at sense port 11 is reconstructed with the same polarity (or zero value) at the input resistor 46.

For illustration of this, assume a positive sense input voltage at sense port 11. Current is caused to flow in resistor 612 into transistor 613 closing relay 400, while transistor 614 does not conduct and relay 500 is open. Current flows from V+ terminal of power supply 64 through resistor 620 into switch 611 (Agreeable) through contact 402C of relay 400 into armature 402A to contact 403C to armature 403 to resistor 46 and variable attenuation resistor 34 for Emotional Independence. On the other hand, if the Attitude switch setting be Contrary, Distrusting, or the like, a negative current flows from the V− terminal of power supply 64 through resistor 621 through switch 611 to relay contact 402C and on as just described. In the sense input is zero, then neither relay 400 or 500 closes and the paths 403C to 403A and 502C to 502 are both open and zero current flows in resistor 46 and variable resistor 34.

If the sense input at 11 is a negative decision force of voltage, then current flows in resistor 612 and transistor 614, closing relay 500 but not relay 400. Then if Attitude switch 611 is set to Agreeable, current flows from V− through resistor 621 to contact 402B to armature 402A to contact 502C to armature 502A to resistor 46 and variable Emotional Independence resistor 34. If Attitude were Contrary then current would flow from V+ through resistor 620 to contact 402B and on as just described to resistor 46 and variable resistor 34 so that a perception force or voltage of opposite positive or negative character from the input influence is generated. In this way the circuitry is configured so that the decision of one individual brings about a decisional influence for a like decision by another individual if the other's attitude is Agreeable, else if Contrary an influence for a different, or opposing, decision. From another point of view the circuitry simulates how one individual distortedly or otherwise perceives the actions of another.

As in FIG. 2B decision port 10 either floats electrically if the individual in simulation is absent from the other, or decision port 10 carries a bipolar voltage due to the connection of resistors 62 and 63 to power supply 64 and contact 101B of relay 100.

The circuitry of FIG. 6 also permits indications of subjective disagreement feelings of one individual toward another. Thus, if the sense input voltage at sense port 11 is positive (Decision of the Woman to Participate), and the decision of the Man is to Avoid, then current flows from V− of the power supply 64 to relay 100 armature 101A to contact 101B (since Man decision was Avoid) to armature 401A of relay 400 to contact 401C (since positive sense input voltage closes relay 400) to lamp 615 in assembly 616, suitably mounted on a display panel such as 1 of FIG. 1, and thence to ground, completing the circuit and causing the lamp 615 to light and indicate a subjective disagreement feeling. However, if the Man decision had been Participate (armature 101A connected to contact 101C), then it is seen that V− has no current path to lamp 615, since there is no disagreement. If Sense input is zero, then there is no connection through either 401 to 401C or 501C and there is no disagreement indication since there is no opposite polarity sensory input force, voltage, or current to "disagree" with.

If the Sense input voltage at sense port 11 is negative (Decision of Woman to Avoid) and the decision of Man is to Participate, then a current path V− to armature 101A to 101C to 501A to 501C to lamp 615 is completed and subjective disagreement of Man is indicated. On the other hand, if decision of Man is to Avoid, then 101A to 101B is conductive but the path is not completed by 401A to 401C to the lamp 615, and the lamp does not light. thus, the circuit of FIG. 6 allows a comparison of the decisions of one idividual with the decisions of another when the other is present, resulting in indications of subjective disagreement when lamp 615 is on and resulting in indications of agreement or absence when lamp 615 is off. The subjective disagreement-agreement circuit of FIG. 6 can be changed into a subjective agreement-disagreement circuit wherein the indications of agreement occur when lamp 615 is on, merely by reversing the connection wires to armatures 401A and 501A. In either case, the indicator registers subjective agreement or disagreement when the positive or negative character of the decisional influence combined total determined by comparison threshold level detector 65 is respectively the same as or opposite from the positive or negative character determined by the sense force polarity determining circuitry 612,613,614,400,500.

Figure 7:
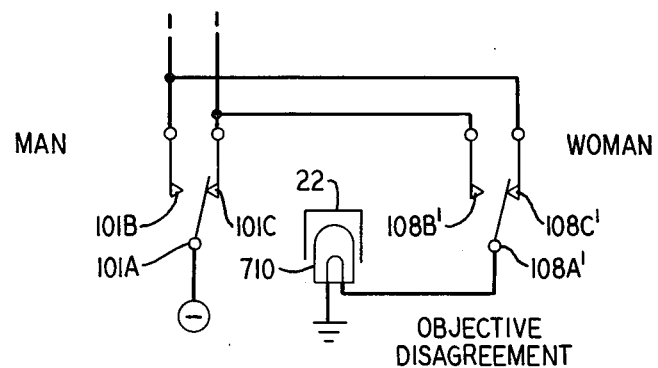
FIG. 7 is a schematic diagram showing how the circuits of FIG. 2B in FIG. 1 may be modified so that the presence of objective disagreement situations between two simulated persons is registered.

A less complex modification to FIG. 2B for indicating disagreement as seen by an outside observer of the relationship (Objective Disagreement) is shown in FIG. 7 modifies FIG. 2B by utilizing a distinct Woman simulator identical with the Man simulator as in FIG. 1, except for having an additional single pole double throw (SPDT) relay contact assembly on Woman simulator relay 100' having a relay armature 108A' and contacts 108B' and 108C'. Armature 108A' is connected to lamp 710 in lamp assembly 22 of FIG. 1 and thence to ground. It will be seen that lamp 710 can only light when the decisions of Man and Woman are opposite, that is, when contact is made from 101A to 101C and 108A' to 108B' (Man-Participate and Woman-Avoid) or from 101A to 101B and 108A' to 108C' (Man-Avoid and Woman-Participate). In this way the illumination of lamp 710 corresponds to objective disagreement between the two individuals regardless of whether each is present to the other or not. Objective agreement is indicated when the lamp 710 is off. Objective agreement indications with lamp 710 on are accomplished by merely reversing the connections to contacts 108B' and 108C'. Even these examples are merely special cases of objective agreement-disagreement circuitry for registering same when the positive or negative combined total decisional influence character determined by comparison amplifier 65 of FIG. 2B relates to a decisional outcome which is respectively the same as or opposite from the one of the Woman decision alternatives corresponding to the polarity of the physical decision force, voltage, or current transmitted to sense port 11.

The practice of the present invention also contemplates alternative, additional or modified circuitry to take account of changes in theoretical psychological and social psychological models of the individual as understanding of the nature of the individual develops. For one very simple example, in the section on "Theory Example", it has been suggested that Like-Dislike is proportional to the relevant personal desire compared with the decision of another person. As shown in equation 26, $L_{12} \propto U_{11}D_2$, so that the personal desire $U_{11}$ determines the magnitude of $L_{12}$ (the intensity of liking or disliking of person 1 for person 2) and the product of $U_{11}$ with the decision $D_2$ determines the sign, or character of the feeling as like or dislike.

However, further reflection and observation may show that the like or dislike magnitude is also proportional to the degree to which the decision of each individual is exerted as a decisional influence upon the other. For example, when another is quite remote, the decisional influence upon one is quite attenuated. However, if another comes much closer or even imposes upon the one to produce stronger decisional influence, the degree of like or dislike is also increased. As an hypothesis like or dislike is set proportional to both personal desire and decisional influence from other according to the relationship $$L_1 \propto U_{11}U_{13} \tag{34}$$

Figure 8:
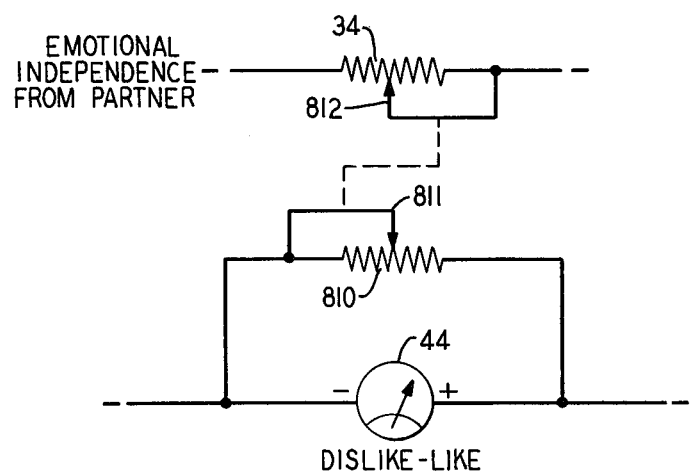
FIG. 8 is a schematic diagram showing a simple example of how the circuit of FIG. 2B may be modified so that the invention may reflect improvements and changes in theories of psychology and emotion.

This relationship may be illustrated in apparatus according to the invention in a variety of ways, a simple approach being a modification of FIG. 2B as shown in FIG. 8. Dislike-Like meter 44 of FIG. 2B is connected as shown in FIG. 2B to take the magnitude of $U_{11}$ into account, as well as the polarity information relating to $U_{13}$. The $U_{13}$ magnitude information is provided by shunting meter 44 with a variable resistor 810 having wiper 811 ganged in opposing sense to the wiper 812 of variable resistor 34 (Emotional Independence from Partner), resistance tapers being chosen to provide the appropriate shunting.

For example, when the Emotional Independence from Partner is low (resistor 34 set to low resistance) then wipers 811 and 812 are set leftward so that the shunt resistance of 810 is high and the meter 44 is free to carry most of the incoming current thereto. If the Emotional Independence from Partner is high, then other's decision has little effect, and wiper 811 is set rightward with wiper 812 so that meter 44 is largely shunted so that even relatively large personal desires $U_{11}$ do not translate into much like or dislike.

In this way FIG. 8 shows how the apparatus of the invention features embodiments corresponding to a variety of theories of personality functioning. In still other examples, FIG. 6 can be modified by making resistors 620 and 621 variable and ganged in the same sense and associated with an adjustment dial for indicating levels of trust and confidence of distrust and lack of confidence; or Subjective Agreement and Disagreement might be indicated as levels in some manner as well; and the like.

Figure 9:
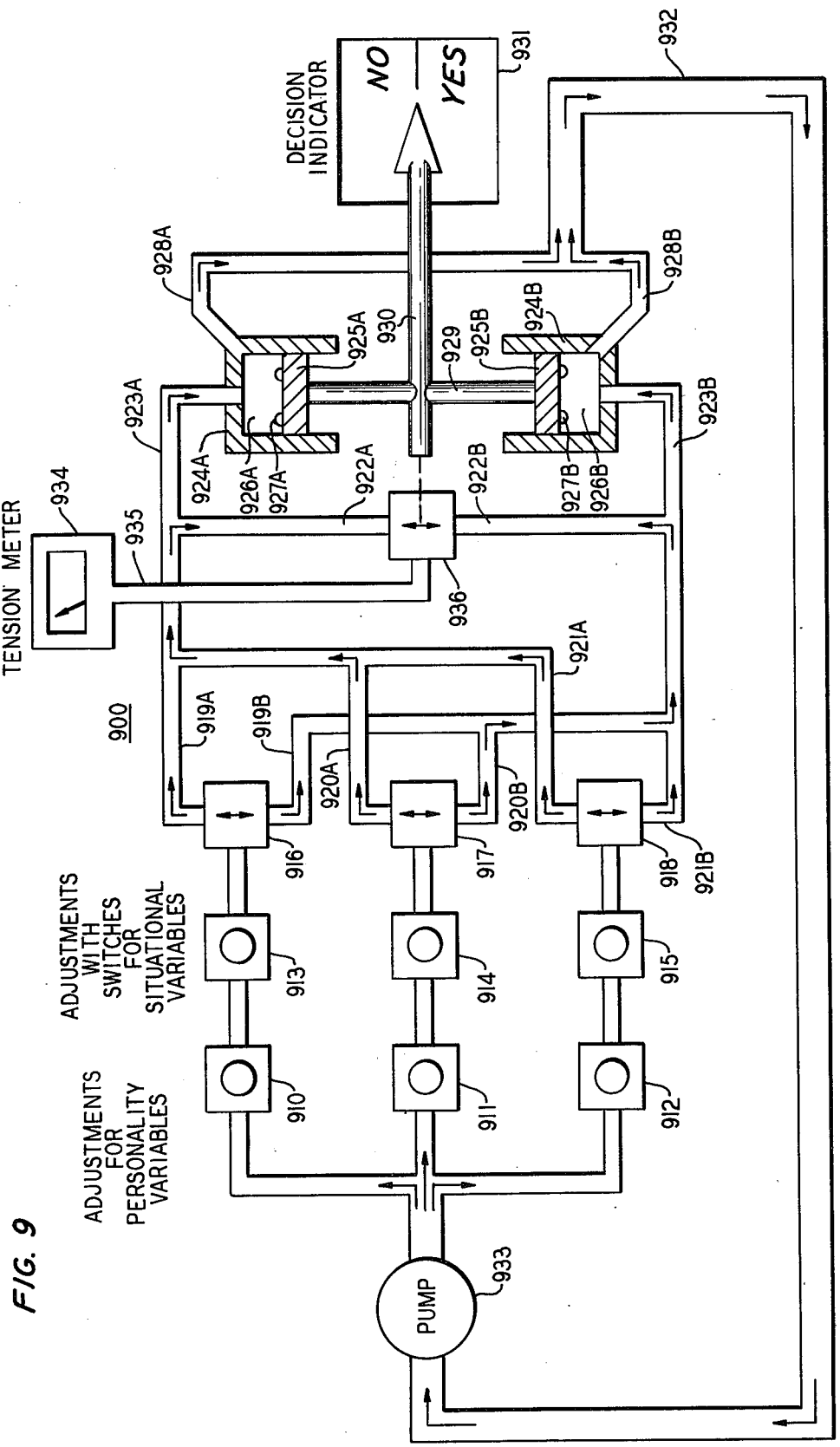
FIG. 9 is a partially block diagrammatic, partially cross-sectional, partially pictorial representation of a fluidic embodiment of the invention for registering emotional tension and simulated decisions.

FIG. 9 illustrates a fluidic embodiment of the present invention, simulator 900. A suitable panel (not shown) features adjustment dial means for personality or isolation decisional influence variables attached to variable fluidic resistances, such as faucets 910,911 and 912; adjustment means for situational variables attached to the continuously adjustable fluidic resistances and fluidic switches such as faucet and tiller (handle) attachments 913,916; 914,917; and 915,918 (the adjustment means respectively having an appearance resembling FIG. 3); Decision Indicator 931, and Nervous Tension Emotion Meter 934.

In a suitable enclosure behind the panel (not shown) pump 933 of suitable conventional type supplies a pressure head of liquid or gaseous fluid to the separate fluidic lines 910,913,916; 911,914,917; and 912,915,918, which operate as sources of physical force or pressure for varying analogs of decisional influence levels. The tiller attachments 916,917, and 918 are arranged so that when a positive type decisional influence, as indicated by at least one of the dials and tillers, is exerted in favor of an illustrative Yes decision, the respective fluidic switch selectably diverts fluid flow into one of fluidic output lines 919A,920A, and 921A for combining in line 923A. Decisional influences of a negative type in favor of a No decision correspond to tiller settings such that the fluidic switches divert fluid flow into alternative lines 919B,920B, and 921B for subsequent combination in line 923B. In this way physical pressure analogs are generated; and although physical pressure is not negative, the apparatus generates a pressure analog to influences having polarity as well as magnitude.

The combined subtotals of Yes and No fluid pressures act on a pair of opposed comparing cylinders 924A and 924B including pistons 925A and 925B connected by common rod 929 and transverse member 930 to run decision indicator 931 and determine whether the combined total of the decisional influences is positive or negative in character. When the Yes pressure in cavity 926A exceeds as a threshold the No pressure in cavity 926B, then the transverse member 930 with indicator arrow is pressed downward to a Yes decision indication; but if the No pressure exceeds the Yes pressure as a threshold, the arrow is pressed up to an alternative No decision indication. Stops 927A and 927B prevent obstruction of fluid flow by pistons 925A and 925B at the ends of their travel. The fluid flows exit the cylinders 924A and 924B through lines 928A and 928B which are preferably connected symmetrically (symmetry not shown for clarity) to return line 932 leading back to Pump 933.

The measurement of emotional tension on fluidic pressure meter 934 is effected by connecting transverse member 930 to a tiller of LESSER fluidic selecting switch 936 such that tension output pressure line 935 to tension meter 934 is connected to the input line 922A or 922B having the lesser combined subtotal pressure. Meter 934 is marked to display magnitudes of a quantity relating to emotional conflict or nervous tension. For example, if the Yes (positive) pressure exceeds to No (negative) pressure (combined total is positive) then transverse member 930 moves downward as explained above, actuates selector switch 936, and connects pressure line 935 to input line 922B, the No line, which has the lesser pressure. In this manner the meter 934 measures as an emotion at least one of the fluidic pressures (when tension exceeds zero) in a manner dependent on the positive or negative character determined by the comparing cylinders, pistons, common rod, and transverse member.

Modifications of the fluidic simulator for more or less than three decisional influence lines will utilize the appropriate number of lines connecting to lines 923A and 923B. In general, the invention comprehends and contemplates fluidic embodiments of a variety of types in addition to the electronic and other embodiments of the invention. FIGS. 10,11,12A, and 12B suggest a variety of mechanicl embodiments of the invention in showing a specific embodiment thereof. It will be noted that the structures shown allow for measurement of simulated emotions, decisionmaking simulation, and physical interaction between simulators of various types in a manner analogous to interpersonal relationships.

Figure 10:
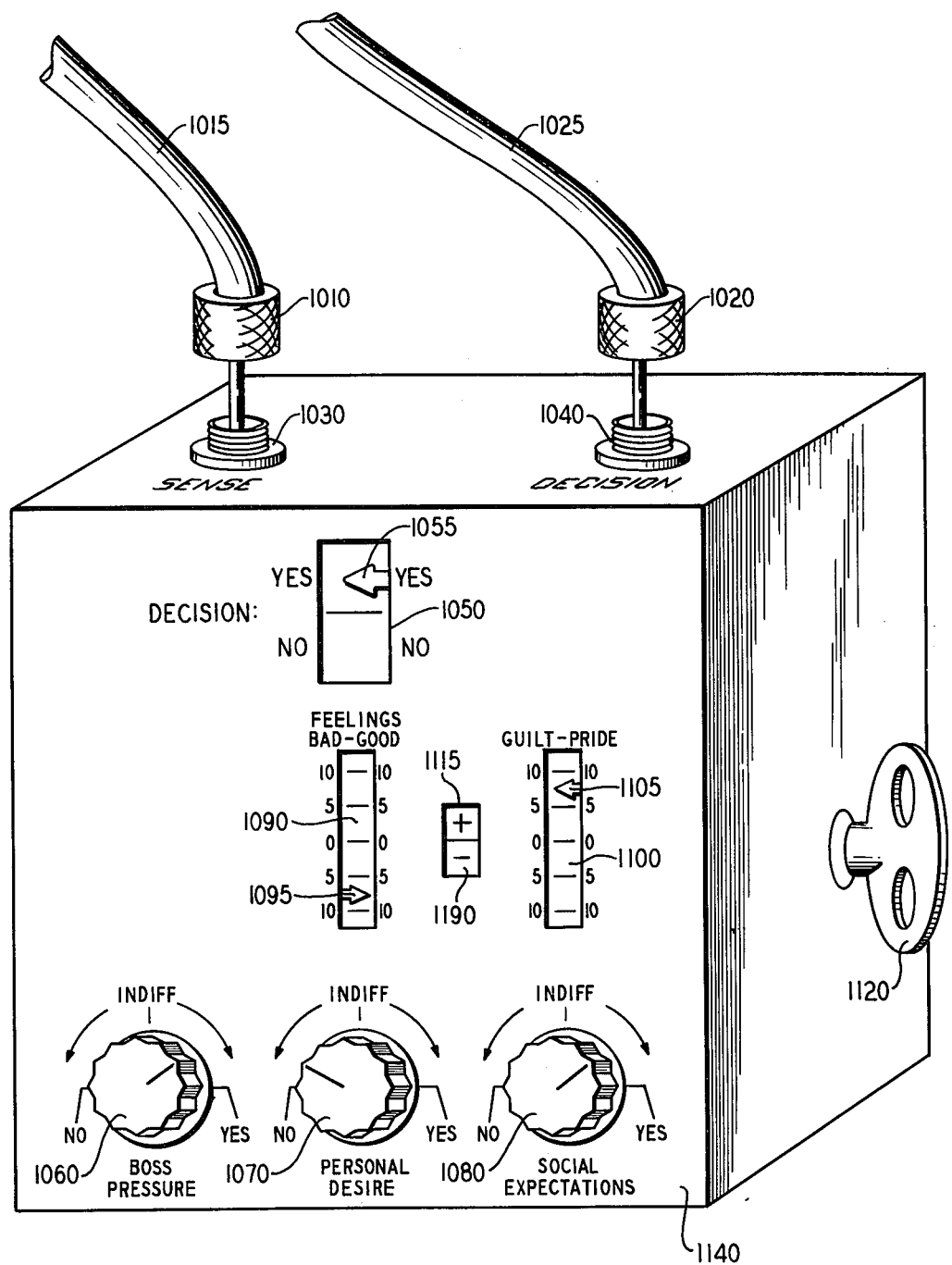
FIG. 10 is a pictorial view of the exterior of an embodiment of the invention in mechanical form for registering emotions and for decisionmaking simulation by itself or in interpersonal simulation with other distinct simulators.

In FIG. 10 adjustment dials 1060,1070, and 1080 on panel 1140 show levels of moderate Boss Pressure for a Yes decision, moderate Personal Desire for a No decision, and Moderate Social Expectations pressure for a Yes decision. These decisional influences can be said to have both polarity, relating to the type of decision favored, and magnitude. The result is that the decisional influences in favor of a Yes decision prevail as indicated by decision indicator 1050 having arrow 1055 pointing in the upper half or Yes portion of the indicator. Since Personal Desire has been thwarted and Social Expectations have been satisfied, it is to be expected that Feelings will be Bad (negative) and Guilt-Pride feelings will be prideful (positive). Mood will be mixed in feelings.

Feelings-Bad-Good indicator 1090 has its arrow 1095 pointing to a negative 7 as determined by reference to the magnitude 7 on the scale and to the sign indicator 115 having tape 1190 showing that below-zero magnitudes are negative and above-zero magnitudes are positive. In a similar manner Guilt-Pride meter 1100 reads positive 7 as shown by arrow 1105 and sign indicator 1115. If, however, the decision indicator 1050 had indicated No, then sign indicator 1115 would show a minus above a plus on tape 1190 in which case the interpretation of the Feelings-Bad-Good and Guilt-Pride would be reversed in sign.

Key 1120 is used to wind up spring-powered mechanical apparatus to be described in connection with FIGS. 12A and 12B later.

Mechanical forces corresponding to the decision reached are transmitted from decision force port 1040 via pushwire cable 1025 affixed to the simulator housing by knurled threaded cuff 1020. The pushwire cable 1025 is suitably attached to another decisionmaking and/or emotion simulator (not shown) like that of FIG. 10, so that forces due to decisions of one simulator are communicated to and impressed on the other and can influence the simulated decisions of the other. In like manner, a decision port of the other simulator (not shown) is connected through pushwire cable 1015 affixed to sense force port 1030 by knurled threaded cuff 1010, the influence the decisions reached by the simulator of FIG. 10.

Figure 11:
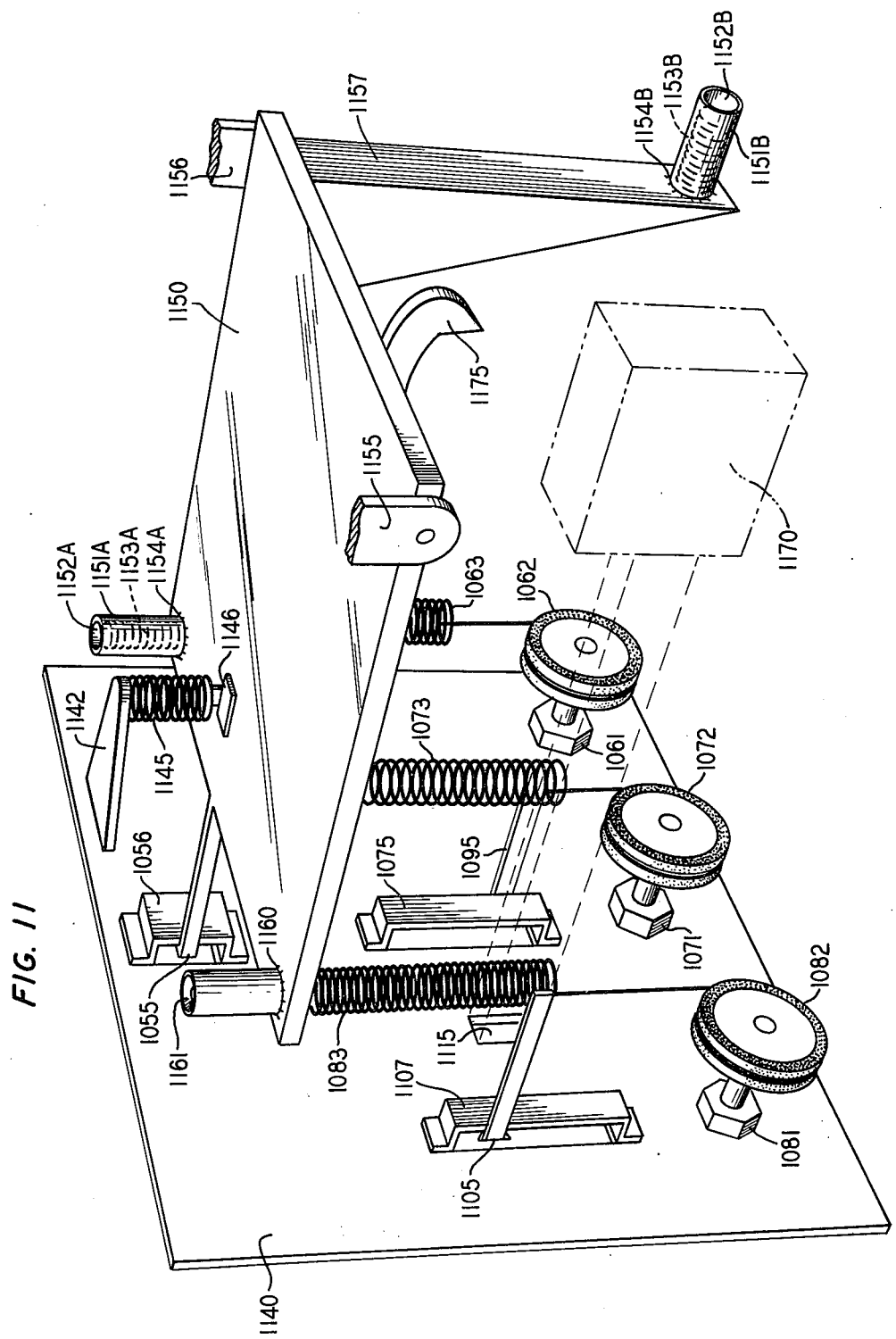
FIG. 11 is a pictorial view of mechanical apparatus for use in the mechanical simulator of FIG. 10, a portion of the apparatus being shown omitted for clarity.

FIG. 11 provides a perspective of the inner mechanical assembly of the simulator seen in exterior view in FIG. 10. Adjustment dials 1060,1070, and 1080 of FIG. 10 are attached to shafts which are held with moderate firmness in fraction bushings 1061, 1071, and 1081 respectively so that torques due to extensions of springs 1063, 1073, and 1083 on takeup wheels 1062, 1072, and 1082 respectively mounted on said shafts cannot influence the adjustment dial settings. However the friction bushings are loose enought to allow convenient adjustment of the dials.

The springs 1063, 1073, and 1083 act as continuously adjustable sources of force relatable to positive and negative decisional influences and provide a variable combined total downward mechanical force on force plate 1150 which is pivoted on bearings 1155 and 1156. This downward force is compared with the threshold type upward force provided by tension spring 1145 mounted by tap 1146 ot force plate 1150 and held by stationary mount 1142. The resulting position of the force plate 1150, which moves when the dials are adjusted, controls the position of arrow 1055 of the decision display indicator 1050 of FIG. 10 having decision scale 1056 and determines whether the combined total of the decisional influences is positive or negative in character.

Emotional indicator arrows 1095 and 1105 extend from the bases of springs 1073 and 1083 to Feelings Bad-Good magnitude scale 1075 and Guilt-pride magnitude scale 1107 respectively. In this way the springs, which can be stretched in their extension independently of each other, influence the emotional level magnitude indications, since the arrows display emotions related to the extensions of the springs. The comparison provided by the force plate influences and actuates the sign indicating assembly 1170 in window 1115 through an escapement claw 1175 by rotation of the force plate 1150 on bearings 1155 and 1156. Assembly 1170 is suggested with phantom technique in FIG. 11 and is fully disclosed in FIGS. 12A and 12B. Thus the apparatus as a whole measures single ones of two physical forces from each of two adjustable force sources in a manner dependent on the positive or negative character determined by the comparing force plate and escapement assembly.

Decision post 1160 having bevel 1161 centers the pushwire cable 1025 of FIG. 10 and adjusts the position of said pushwire so as to move it as the force plate 1150 moves, thereby transmitting a decisional force to a distinct simulator.

Pushwire forces are received from another simulator in a manner relatable to a bipolar decisional influence at either of posts 1151A or 1151B, the pushwire connection being made depending on whether the influence simulated is to be of a contrary or presuasive (agreeable) type respectively. This is because a downward (Yes) force at 1151A acts in the opposite direction to the decision (Yes-force plate up) which would generate it, yielding a contrary influence, while a similar force on 1151B would yield an upward (Yes) force in the same direction as the decision (Yes-force plate up) which would generate it.

Each of the hollow cylindrical receiving posts 1151A and 1151B are respectively joined to force plate 1150 and force lever bar 1157 by welds 1154A and 1154B, and have springs 1153A and 1153B hidden inside fitted with movable contact bevel receiving tabs 1152A and 1152B, not shown, for contacting a pushwire.

Figure 12B:
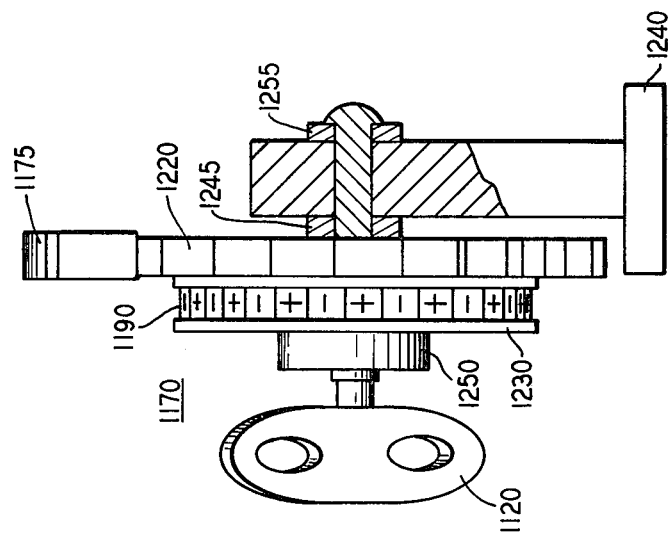
FIGS. 12A and 12B are front and side elevation views of escapement apparatus used in the mechanical apparatus of FIG. 11, but for clarity omitted therefrom.
Figure 12A:
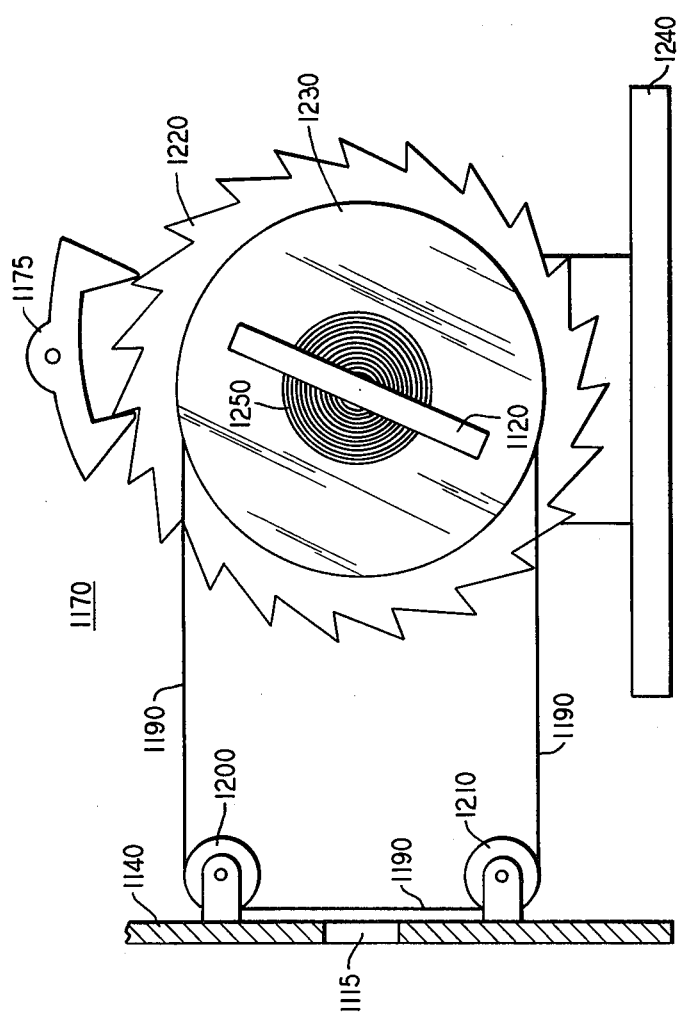

FIGS. 12A and 12B show in front and profile views respectively the sign indicator assembly 1170 suggested in phantom in FIG. 11. These figures are described together hereinbelow.

Alternating decisions corresponding to the alternating motions of force plate 1150 of FIG. 11 cause alternations of escapement claw 1175 on toothed wheel 1220. In turn, spring torque due to spring 1250 would up by key 1120 forces sudden counterclockwise angular motion of toothed wheel 1220 and reel 1230 on an axle held with bushings 1245 and 1255 to solid base 1240. The sudden motion corresponds to actuations of escapement assembly 1170 when the decision changes from No to Yes and vice-versa.

Tape 1190 correspondingly advances in window 1115 by the turning of reel 1230. The tape is brought near sign indicator window 1115 in panel 1140 with the aid of freely turning tape wheels 1200 and 1210. Tape 1190 has endless markings of − + − + − +. In this way the comparison of the spring tensions in springs 1063,1073, and 1083, which are relatable to positive and negative decisional influences, is translated into an emotional type or sign indication which when taken together with the emotional magnitude indications at 1090 and 1100 of FIG. 10 make possible complete means of measuring and indicating emotions of panel 1140.

It is to be understood, of course, that the invention comprehends numerous embodiments. It is within the scope of the invention that digital and memory techniques and the use of inexpensive microprocessors or other state-of-the-art circuit and calculating techniques offering manufacturing and cost advantages can provide alternative advantageous means of practicing the invention in a manner different in form from the herein disclosed embodiments but consistent in substance with the present invention. Other contemplated apparatus of the invention includes means of having a simulator operate its own adjustment means such as by servomechanisms or other means in response to decision port voltages when the subject decision alternatives relate, for instance, to improving one's own personality, internalizing social expectations for the first time, or becoming more or less dependent on others for example. In any event, the invention comprehends numerous embodiments in a variety of physical systems of analogous, hybrid, digital, and modified type and the choice of construction may be made by persons skilled in the art in any manner for providing suitable embodiments adapted for the purposes at hand, by applying the principles disclosed herein.

I claim
1. Simulation apparatus comprising
a plurality of sources of respective physical forces, at least one of said force sources being substantially continuously adjustable in level, said forces being relatable to levels of positive and negative decisional influences;
means for comparing said physical forces so as to determine whether a combined total of levels of at least two of said decisional influences is positive or negative in character; and
means for indicating one or more simulated emotions, each simulated emotion having a range of simulated emotional levels, by measuring as an emotion at least one of said physical forces including a force from at least one said adjustable force source in a manner dependent on the positive or negative character determined by said comparing means.

2. Simulation apparatus as claimed in claim 1 wherein said emotional level indicating means indicates emotional levels by measuring single respective ones of said physical forces each relating to a respective simulated emotion.

3. Simulation apparatus as claimed in claim 1 wherein said apparatus further comprises means for indicating one at a time of a plurality of decisions, said decision indicator indicating one decision when said combined total of levels is positive in character and indicating another decision when said combined total of levels is negative in character.

4. Simulation apparatus as claimed in claim 3 wherein each said adjustable physical force source is adjustable by adjustment means including adjustment dial means for indicating levels of a respective one of said decisional influences.

5. Simulation apparatus as claimed in claim 1 wherein each said adjustable physical force source is adjustable by adjustment means including adjustment dial means for indicating levels of a respective one of said decisional influences.

6. Simulation apparatus as claimed in claim 5 wherein one said adjustment dial means indicates levels of a decisional influence relating to personal desire, and said emotional level indicating means includes means for indicating levels of feelings about oneself substantially proportional to said decisional influence relating to personal desire, said feelings levels being positive when said combined total of the decisional influences is of the same positive or negative character as said personal desire decisional influence.

7. Simulation apparatus as claimed in claim 6 wherein said feelings levels are negative when said combined total of the decisional influences is of the opposite positive or negative character from said personal desire decisional influence.

8. Simulation apparatus as claimed in claim 6 wherein
said sources of physical force comprise electrical sources having said adjustment means associated therewith, said electrical sources providing electrical influences respectively having levels having polarities corresponding to said positive and negative decisional influences,
said personal desire adjustment dial means adjusting a corresponding electrical influence,
said emotional level indicator means including electrical meter means being polarity reversible and coupled to said personal desire electrical influence for measuring same,
said comparing means including means for reversing the polarity of said meter means when said combined total of levels changes in character.

9. Simulation apparatus as claimed in claim 5 wherein one said adjustment dial means indicates levels of a decisional influence relating to social pressure, and said emotional level indicating means includes means for indicating levels of an emotion related to social estimation perceived by oneself, said emotional levels being substantially proportional to said decisional influence relating to social pressure, said social estimation emotional levels being positive when said combined total of the decisional influences is of the same positive or negative character as said social pressure decisional influence.

10. Simulation apparatus as claimed in claim 9 wherein
said sources of physical force comprise electrical sources having said adjustment means associated therewith, said electrical sources providing electrical influences respectively having levels having polarities corresponding to said positive and negative decisional influences,
said social pressure adjustment dial means adjusting a corresponding electrical influence,
said emotional level indicator means including electrical meter means being polarity reversible and coupled to said social pressure electrical influence for measuring same,
said comparing means including means for reversing the polarity of said meter means when said combined total of levels changes in character.

11. Simulation apparatus as claimed in claim 5 wherein
one said adjustment dial means indicates levels of a decisional influence relating to social pressure, and
said emotional level indicating means includes means for indicating levels of an emotion related to social estimation perceived by oneself, said emotional levels being substantially proportional to said decisional influence relating to social pressure, said social estimation emotional levels being negative when said combined total of the decisional influences is of the opposite positive or negative character from said social pressure decisional influence.

12. Simulation apparatus as claimed in claim 11 wherein said apparatus further comprises means for substantially disabling said social estimation emotional level indicating means, said disabling means having switchable indications relating to internalization or not of social expectations.

13. Simulation apparatus as claimed in claim 5 wherein
one said adjustment dial means indicates levels of a decisional influence relating to personal desire of an individual, and
said emotional level indicating means includes means for indicating levels of an emotion relating to liking by said individual of at least one other entity, said liking levels being substantially proportional to said decisional influence relating to personal desire, said liking levels being positive when said personal desire is of the same positive or negative character as said combined total of the decisional influences where the comparing means compares forces relatable to levels of positive and negative decisional influences on each said other entity.

14. Simulation apparatus as claimed in claim 13 wherein
said sources of physical force comprise electrical sources having said adjustment means associated therewith, said electrical sources providing electrical influences respectively having levels having polarities corresponding to said positive and negative decisional influences,
said personal desire adjustment dial means adjusting a corresponding electrical influence,
said emotional level indicator means including electrical meter means being polarity reversible and coupled to said personal desire electrical influence for measuring same, said comparing means including means for reversing the polarity of said meter means when said combined total of levels changes in character.

15. Simulation apparatus as claimed in claim 14 wherein said comparing means further comprises means for substantially disabling said liking emotional level indicating means in the absence of a comparing means determination, said absence being analogous to absence of each said entity.

16. Simulation apparatus as claimed in claim 13 wherein said apparatus further comprises means for enabling the indication of said levels of liking to also be substantially proportional to at least one force relatable to the magnitude of a decisional influence due to each said other entity.

17. Simulation apparatus as claimed in claim 5 wherein
one said adjustment dial means indicates levels of a decisional influence relating to personal desire of an individual, and
said emotional level indicating means includes means for indicating levels of an emotion relating to dislike or fear by said individual of at leat one other entity, said dislike or fear levels being substantially proportional to said decisional influence relating to personal desire, said dislike or fear levels being positive in magnitude when said personal desire is of the opposite positive or negative character from said combined total of the decisional influences where the comparing means compares forces relatable to levels of positive and negative decisional influences on each said other entity.

18. Simulation apparatus as claimed in claim 1 wherein said emotional level indicating means includes means for indicating a quantity relating to emotional conflict or nervous tension, said quantity being substantially proportional in magnitude to a combined subtotal of the levels of said decisional influences which are negative when said comparing means determines a positive character and being substantially proportional in magnitude to a combined subtotal of the levels of said decisional influences which are positive when said comparing means determines a negative character, said determining of said comparing means being substantially equivalent to determining which of said subtotals is lesser in magnitude.

19. Simulation apparatus as claimed in claim 18 wherein said sources of physical force comprise electrical sources having adjustment means associated therewith.

20. Simulation apparatus as claimed in claim 19 wherein
said electrical sources provide electrical influences respectively having levels having polarities corresponding to said positive and negative decisional influences,
said comparing means includes threshold level detector means connected at an input to said electrical sources and connected at an output to selecting means, and
said emotional level indicating means includes electrical meter means connected in a way selected by said selecting means to one at a time of a plurality of combining means for providing respective subtotals of said electrical influences,
whereby said meter means indicates said quantity relating to emotional conflict or nervous tension.

21. Simulation apparatus as claimed in claim 20 wherein said selecting means is relay means having contact assembly means for selecting connections to said single-polarity subtotals combining means.

22. Simulation apparatus as claimed in claim 20 wherein
said plurality of subtotals combining means comprises diodes connecting each of said sources of electrical influence to a positive polarity resistive path and reverse-connected diodes connecting each of said sources of electrical influence to a negative polarity resistive path, and
said meter means is connected to one at a time of said resistive paths by said selecting means.

23. Simulation apparatus as claimed in claim 20 wherein
said adjustment means includes dial means for indicating magnitudes of respective decisional influences and switches for choosing and indicating decisional influence types of choosing electrical influence polarities of said electrical sources;
said plurality of subtotals combining means comprises a switching network including switches ganged to said adjustment means switches, said network selectably connecting each of said electrical sources to a positive polarity resistive path and to a negative polarity resistive path depending on the respective electrical influence polarity chosen for each of said sources; and
said meter means is connected to one at a time of said resistive paths by said selecting means.

24. Simulation apparatus as claimed in claim 19 wherein
said electrical sources provide electrical influences respectively having levels having polarities corresponding to positive and negative decisional influences,
said force sources further comprise
a plurality of combining means for providing respective subtotals of said electrical influences of each polarity, and
means for providing electrical outputs of identical polarity to each other, each output being proportional in magnitude to said subtotals, and
said comparing means includes means for selecting the electrical output of lesser magnitude for measuring by said emotional level indicating means,
whereby said emotional level indicating means indicates said quantity relating to emotional conflict or nervous tension.

25. Simulation apparatus as claimed in claim 24 wherein said plurality of subtotals combining means comprises diodes connecting each of said sources of electrical influence to a positive polarity resistive path and reverse-connected diodes connecting each of said sources of electrical influence to a negative polarity resistive path, and
each said resistive path is connected to said means for providing electrical outputs.

26. Simulation apparatus as claimed in claim 24 wherein
said adjustment means includes dial means for indicating magnitudes of respective decisional influences and switches for choosing and indicating decisional influence types by choosing electrical influence polarities of said electrical sources;
said plurality of subtotals combining means comprises a switching network including switches ganged to said adjustment means switches, said network selectably connecting each of said electrical sources to a positive polarity resistive path and to a negative polarity resistive path depending on the respective electrical influence polarity chosen for each of said sources; and each said resistive path is connected to said means for providing electrical outputs.

27. Simulation apparatus as claimed in claim 24 wherein said means of providing electrical outputs of identical polarity comprises chopper means provided with said respective subtotals, AC amplifier means fed by said chopper means, and peak detector means fed by said AC amplifier means, said peak detector means providing each said identical polarity output.

28. Simulation apparatus as claimed in claim 27 wherein said plurality of subtotals combining means comprises diodes connecting each of said sources of electrical influence to a positive polarity resistive path and reverse-connected diodes connecting each of said sources of electrical influence to a negative polarity resistive path, and each said resistive path is connected to said means for providing electrical outputs.

29. Simulation apparatus as claimed in claim 24 wherein said selecting means comprises diodes connected to each said identical polarity output and to a common junction connected in turn to said emotional level indicating means.

30. Simulation apparatus as claimed in claim 24 wherein said apparatus further comprises threshold level detector means connected at an input to said electrical sources and connected at an output to decision indicator means displaying one at a time of a plurality of decisions.

31. Simulation apparatus as claimed in claim 18 wherein said sources of physical force comprise fluidic pump means connected to a plurality of lines having adjustable faucets and fluidic switch means for selecting alternative fluidic output lines corresponding to said positive and negative decisional influences, said faucets varying said decisional influences in level and said switch means adjusting said decisional influences in polarity.

32. Simulation apparatus as claimed in claim 31 wherein said comparing means comprises a pair of cylinders connected respectively to said positive switch output lines and said negative switch output lines, said cylinders each having a piston connected by a common rod each to each, said common rod being connected to LESSER fluidic switch selecting means having input lines respectively connected to said positive and negative switch output lines so as to connect the lesser pressure switch output line to said emotional level indicating means comprising a fluidic pressure meter marked to display magnitudes of fluid quantity relating to emotional conflict or nervous tension.

33. Simulation apparatus as claimed in claim 32 wherein said common rod is also connected to decisional indicator means displaying one of a plurality of decisional outcomes.

34. Simulation apparatus as claimed in claim 1 wherein each said adjustable physical force source is adjustable by adjustment means including adjustment dial means for indicating levels of a respective one of said decisional influences, there being at least first and second continuously adjustable force sources having associated respectively therewith for said first force source, adjustment dial means for indicating decisional influence levels relating to personal desire and adjustment dial means for indicating decisional influence levels relating to isolation from or compliance with said personal desire associated with attenuation means in said first force source; and for said second force source, adjustment dial means for indicating decisional influence levels relating to social pressure and adjustment dial means for indicating decisional influence levels relating to isolation from or compliance with said social pressure associated with attenuation means in said second force source.

35. Simulation apparatus as claimed in claim 1 wherein each said adjustable physical force source is adjustable by adjustment means including adjustment dial means for indicating levels of a respective one of said decisional influences, said apparatus further comprising means for providing a variety of situational interpretations to said adjustment dial means.

36. Simulation apparatus as claimed in claim 35 wherein said interpretational means comprises a plurality of interchangeable overlay sheets providable to a panel having said adjustment dial means.

37. Simulation apparatus as claimed in claim 1 wherein said apparatus further comprises a sense port for receiving a sensed physical force;

means for variably attenuating said sensed physical force; and adjustment dial means for adjusting said variable attenuating means and indicating levels relating to emotional independence from another entity, said physical force so attentuated being fed to said comparing means.

38. Simulation apparatus as claimed in claim 1 wherein said apparatus further comprises a sense port for receiving a sensed physical force relatable to a perception of another entity by an individual;

adjustment means for indicating one or more attitudes of the individual, and perceptual processing means utilizing said sensed physical force in a manner adjustable by said attitude adjustment means so as to influence the indication of said emotional level indicating means.

39. Simulation apparatus as claimed in claim 1 wherein said apparatus further comprises a sense port for receiving a sensed physical force having a polarity;

means for determining said polarity; and means for indicating one or more simulated emotions, each said simulated emotion having a range of simulated emotional levels, by measuring at least one of said physical forces including a force from at least one said adjustable force source in a manner dependent on the positive or negative character determined by said sensed force polarity determining means.

40. Simulation apparatus as claimed in claim 39 wherein said apparatus further comprises adjustment means for indicating one or more attitudes of an individual, and means adjustable by said attitude adjustment means for reversing polarity determination of the sensed force polarity determining means.

41. Simulation apparatus as claimed in claim 40 wherein said apparatus utilizes electrical force sources, is adapted to receive a sensed electrical force at said sense port, said attitude adjustment means indicates attitude alternatives relating to Contrary and Agreeable, and said means for indicating one or more simulated emotions includes like-dislike emotional level electrical meter means measuring a physical force relatable to personal desire decisional influence, said like-dislike meter means being reversible in polarity in a manner dependent on the positive or negative character determined by said sensed force polarity determining means.

42. Simulation apparatus as claimed in claim 39 wherein said apparatus further comprises subjective substantial agreement or disagreement indicator means for registering subjective agreement or disagreement when the positive or negative character determined by said comparing means is respectively the same as or opposite from said positive or negative character determined by said sensed force polarity determining means.

43. Simulation apparatus as claimed in claim 1 wherein said simulation apparatus communicates with a distinct simulator capable of transmitting a physical force to said simulation apparatus for comparison by said comparing means.

44. Simulation apparatus as claimed in claim 43 wherein said distinct simulator includes means for interrupting said physical force so as to simulate presence or absence of an individual simulated by said distinct simulator.

45. Simulation apparatus as claimed in claim 43 wherein said distinct simulator is a decision making simulator producing a physical force having polarity corresponding to decision alternatives and said simulation apparatus further comprises objective agreement-disagreement indicator means for registering same when the positive or negative character determined by said comparing means relates to a decisional outcome which is respectively the same as or opposite from the one of said decisional alternatives corresponding to the polarity of said physical force.

46. Simulation apparatus as claimed in claim 1 wherein said simulation apparatus further comprises means for producing a decisional output force having a positive or negative character dependent on said determination of said comparing means, said output force being available at a decision port.

47. Simulation apparatus as claimed in claim 46 wherein said simulation apparatus further comprises means for interrupting said decisional output force associated with means for switchably essentially indicating the presence or absence of a simulated individual.

48. Simulation apparatus as claimed in claim 46 wherein
said decisional output force has alternative polarities, and
said simulation apparatus comprises means for reversing the polarity dependence of said decisional output for one said determination of said comparing means associated with means for essentially switchably indicating contrary or agreeable influence.

49. Simulation apparatus as claimed in claim 46 wherein
the decisional output force available at said decision port is communicated to second emotion or decisionmaking simulation apparatus so as to act as a decisional influence thereon.

50. Simulation apparatus as claimed in claim 1 wherein said simulation apparatus further comprises
means for producing a first decisional output force having a positive or negative character dependent on said determination of said comparing means;
a second plurality of sources of respective physical forces, at least one of said second force sources being substantially continuously adjustable in level, said forces being relatable to levels of positive and negative decisional influences;
second means for comparing said second physical forces so as to determine whether a combined total of levels of at least two decisional influence forces is positive or negative in character; and
second means for indicating one or more simulated emotions, each simulated emotion having a range of simulated emotional levels, by measuring at least one said physical force including a force from at least one said second adjustable force source in a manner dependent on the positive or negative character determined by said second comparing means;
said first decisional output force being relatable to a first decisional influence due to a decision of a first individual and being fed to said second comparing means,
whereby emotions in interpersonal relationships are able to be simulated.

51. Simulation apparatus as claimed in claim 50 wherein said apparatus further comprises
second means for producing a second decisional output force having a positive or negative character dependent on said determination of said second comparing means,
said second decisional output force being relatable to a second decisional influence due to a decision of a second individual and being fed to said first comparing means,
whereby emotions in reciprocal interpersonal relationships are able to be simulated.

52. Simulation apparatus as claimed in claim 51 wherein
said plurality of force sources comprise electrical first potentiometers connected across a dual polarity power supply, said potentiometers being attached to adjustment dials for indicating decisional influences relating to personal desire and social pressure for a first individual, said potentiometers having wipers connected to respective first variable isolation resistors attached to adjustment dials for essentially indicating independence from personal desire and social pressure of said first individual,
said variable resistors being connected to first emotion meter shunt resistors in turn connected to forward-connected first diodes connected to a first positive summation resistor, said shunt resistors also in turn being connected to reverse-connected first diodes connected to a first negative summation resistor, said first positive and negative summation resistors being connected to a first threshold level detector being in turn connected to a first selector relay acting as said first comparing means, and
said first emotion indicator means comprises
guilt-pride electrical meter means connected by a polarity-reversing contact assembly on said first selector relay to one of said meter shunt resistors ultimately connected to said social pressure potentiometer wiper, bad-good feelings electrical meter means connected by a polarity-reversing contact assembly on said first selector relay to one of said meter shunt resistors ultimately connected to said personal desire potentiometer wiper, and tension emotion electrical meter means connected by a contact assembly on said first selector relay to said positive and negative summation resistors so that the magnitude of the lesser current in said summation resistors is displayed on said meter at all times, said second plurality of force sources, said second comparing means and said second emotion indicator means are of a type as recited for their first counterparts hereinabove, and said first and second selector relays have first and second contact assemblies connected to said dual polarity power supply for generating first and second dual polarity decisional output voltages which in turn are applied to second and first variable resistors attached to second and first emotional independence adjustment dials, said second and first variable resistors in turn being ultimately connected to said second and first threshold level detectors respectively.

53. Simulation apparatus as claimed in claim 1 wherein said sources of force respectively provide mechanical forces respectively relatable to positive and negative decisional influences.

54. Simulation apparatus as claimed in claim 53 wherein said sources of mechanical force include springs adjustable in extension by adjustment dial means;

said comparing means is a force plate connected to said springs so that the combined total of said forces is exerted on said force plate and said plate moves in position in a manner determinative of the corresponding positive or negative character of said combined total of said decisional influences, and said emotional level indicating means displays a magnitude related to an extension of at least one of said springs and a sign dependent upon the position of said plate.

55. Simulation apparatus as claimed in claim 54 wherein one said adjustment dial means indicates polarities and levels of personal desire and adjusts the extension of a personal desire spring and said emotional level indicating means indicates an emotion relating to good-bad feelings related in magnitude to the extension of said personal desire spring and in sign according as the position of said plate corresponds to a positive or negative character of said combined total of said decisional influences identical with the polarity of said personal desire indicated by said adjustment dial.

56. Simulation apparatus as claimed in claim 54 wherein one said adjustment dial means indicates polarities and levels of a form of social expectations and adjusts the extension of a social expectations spring and said emotional level indicating means indicates an emotion relating to guilt-pride feelings related in magnitude to the extension of said social expectations spring and in sign according as the position of said plate corresponds to a positive or negative character of said combined total of said decisional influences identical with the polarity of said form of social expectations indicated on said adjustment dial.

57. Simulation apparatus as claimed in claim 54 wherein said plate by its motion actuates escapement means for advancing emotional sign display means included in said emotional level indicating means so as to permit said emotional sign to be displayed dependent on the position of said plate.

58. Simulation apparatus as claimed in claim 54 wherein said apparatus further comprises means for displaying one at a time of a plurality of decisional outcomes related to said decisional influence combined total, said displaying means being operated by the motion of said plate.

59. Simulation apparatus as claimed in claim 54 wherein said apparatus further comprises force port means for permitting communication of force to and from said plate whereby simulation of interpersonal relationships is facilitated.

60. Simulation apparatus comprising a pump;

a plurality of fluid lines connected to said pump, said lines containing adjustable fluidic resistance means;

fluidic switch means connected to said fluidic resistance means so that the fluid flow takes one of at least two alternate paths corresponding to alternative decisional influence types;

decisional influence adjustment and indication means associated with said fluidic resistance and fluidic switch means;

means for indicating an emotional variable, said indicating means being connected to one or more of said alternate paths;

and means for comparing the fluid flow in said alternative paths and providing a decision indication therefrom.

61. Simulation apparatus as claimed in claim 60 wherein said emotional variable indicating means is a fluid pressure meter connected to fluidic selector switch means, said fluidic selector switch means being connected to lines to each of two of said alternate paths, said fluidic selector being actuated by said comparing means so as to connect said pressure meter to the alternate path having the lesser fluid pressure.

62. Simulation apparatus comprising means for indicating and adjustably varying levels of a plurality of decisional influences;

means for indicating one of a plurality of alternative decisions;

and physical system means for (A) causing said decision indicator means to indicate a first decision when a combined total of at least come of said variable levels is above a threshold level and to indicate a different decision when said total is below said threshold level and (B) deriving and indicating at least one simulated emotional level dependent upon at least one of said decisional influence levels and upon whether said combined total is above or below said threshold level.

63. Simulation apparatus as claimed in claim 62 wherein said physical system means comprises adjustable means for producing a plurality of electrical currents, said producing means being adjustable by said adjustable decisional influence indicating means; and said physical system means also comprises meter means for measuring at least a portion of one or more of said electrical currents and indicating in terms of at least one simulated emotional level, said meter means being automatically and selectively connectable in said physical system means.

64. Simulation apparatus as claimed in claim 63 wherein said emotion meter means is reversibly connectable in polarity in said physical system means.

65. Simulation apparatus as claimed in claim 63 wherein said physical system means further comprises level detector means responsive to a combined total of said electrical currents, said decision indicator means being responsive to said level detector; and means responsive to said level detector for selectively changing the connection of said emotion meter means in said physical system means when said decision indication changes.

66. Simulation apparatus as claimed in claim 65 wherein said selective connection means reverses the connection of said emotion meter means in said physical system means when said decision changes.

67. In a method for deriving emotional indications in a simulation apparatus, the steps comprising generating a first physical analog of a decisional influence having a first magnitude and polarity;

generating a second physical analog of a decisional influence having a second magnitude and polarity;

comparing said physical analogs so as to determine whether a combined total of said decisional influences is positive or negative in character; and producing an emotional analog and indicating it to have a magnitude and sign depending on said first or second magnitude and said positive or negative character determined for said combined total.

68. Simulation apparatus for deriving emotional indications by the method of claim 67.

69. In a method for deriving emotional indications in a simulation apparatus, the steps comprising generating a first physical analog of a decisional influence having a first magnitude and polarity;

generating a second physical analog of a decisional influence having a second magnitude and polarity;

producing a combined total of all negative polarity magnitudes and a combined total of all positive polarity magnitudes;

selecting the lesser magnitude of said combined totals; and indicating said lesser magnitude as an emotion.

70. Simulation apparatus for deriving emotional indications by the method of claim 69.

* * * * *

UNITED STATES PATENT OFFICE
CERTIFICATE OF CORRECTION

Patent No. 4,041,617            Dated August 16, 1977

Inventor(s) James Fisher Hollander

It is certified that error appears in the above-identified patent and that said Letters Patent are hereby corrected as shown below:

Column 8, line 38, "fell" should read --feel--.
Column 9, line 1, "cabiner" should read --cabinet--.
Column 9, line 42, "$P_1=U_{12}D_1=X1=1$" should read --$P_1=U_{12}D_1=1x1=1$--
Column 11, line 26, "on" should read --one--.
Column 13, line 50, "suppy" should read --supply--.
Column 16, line 62, "$i_{11}$" should read --$I_{11}$--.
Column 16, line 6, "non" should read --no--.
Column 17, line 4, "$i_{11}$" should read --$I_{11}$--.
Column 18, line 7, "the" should read --to-- and "of" should read --or--.
Column 18, line 15, "R" should read --R38--.
Column 18, line 16, "R→" should read --R43-- and "R/" should read --R51--.
Column 18, line 17, "10,00" should read --10,000--.
Column 19, line 54, "nd" should read --and--.
Column 20, line 25, "of" should read --or--.
Column 20, line 53, "of" should read --or--.
Column 21, line 58, after "FIG. 7" insert --. FIG.7--.
Column 24, line 68, "the" should read --to--.
Column 25, line 7, "fraction" should read --friction--.

UNITED STATES PATENT OFFICE

CERTIFICATE OF CORRECTION

Patent No. 4,041,617      Dated August 16, 1977

Inventor(s)    James Fisher Hollander

It is certified that error appears in the above-identified patent and that said Letters Patent are hereby corrected as shown below:

Column 25, line 21, "tap" should read --tab-- and "ot" should read --to--.

Column 30, line 20, in sixth line of claim 23 "types of" should read --types by--.

Column 31, lines 62,63 in lines 2 and 3 of claim 33 "decisional" should read --decision--.

Column 32, line 26, in second line of claim 36 "interpretational" should read -- interpretation --.

Column 36, line 56, in line 8 of claim 62 "come" should read -- some --.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks